United States Patent
Steinmetz et al.

(10) Patent No.: US 10,385,321 B2
(45) Date of Patent: Aug. 20, 2019

(54) MRP-14 TARGETING PEPTIDES AND USES THEREOF

(71) Applicant: CASE WESTERN RESEVE UNIVERSITY, Cleveland, OH (US)

(72) Inventors: Nicole F. Steinmetz, Cleveland, OH (US); Amy M. Wen, Cleveland, OH (US); Daniel Simon, Cleveland, OH (US); Yunmei Wang, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/615,458

(22) Filed: Jun. 6, 2017

(65) Prior Publication Data
US 2017/0348438 A1    Dec. 7, 2017

Related U.S. Application Data

(60) Provisional application No. 62/345,939, filed on Jun. 6, 2016.

(51) Int. Cl.
*B82Y 5/00* (2011.01)
*C12N 7/00* (2006.01)
*A61K 47/64* (2017.01)
*A61K 47/69* (2017.01)

(52) U.S. Cl.
CPC ............... *C12N 7/00* (2013.01); *A61K 47/64* (2017.08); *A61K 47/6901* (2017.08); *B82Y 5/00* (2013.01); *C12N 2770/00023* (2013.01)

(58) Field of Classification Search
None
See application file for complete search history.

(56) References Cited

U.S. PATENT DOCUMENTS

2016/0297875 A1* 10/2016 Simon ............... G01N 33/6893

OTHER PUBLICATIONS

New England Biolabs, Data Sheet for Ph.D.TM-C7C Phage Display Library, for product expiring Sep. 2014. Downloaded from www.neb.com (Year: 2014).*

* cited by examiner

*Primary Examiner* — Christina Bradley
(74) *Attorney, Agent, or Firm* — Tarolli, Sundheim, Covell & Tummino LLP

(57) ABSTRACT

A peptide for targeting MRP-14 has an amino acid sequence at least 80% identical to amino acid sequence selected from the group consisting of SEQ ID NO: 2, SEQ ID NO: 3, SEQ ID NO: 5, SEQ ID NO: 6, SEQ ID NO: 9, and SEQ ID NO: 10.

21 Claims, 13 Drawing Sheets
Specification includes a Sequence Listing.

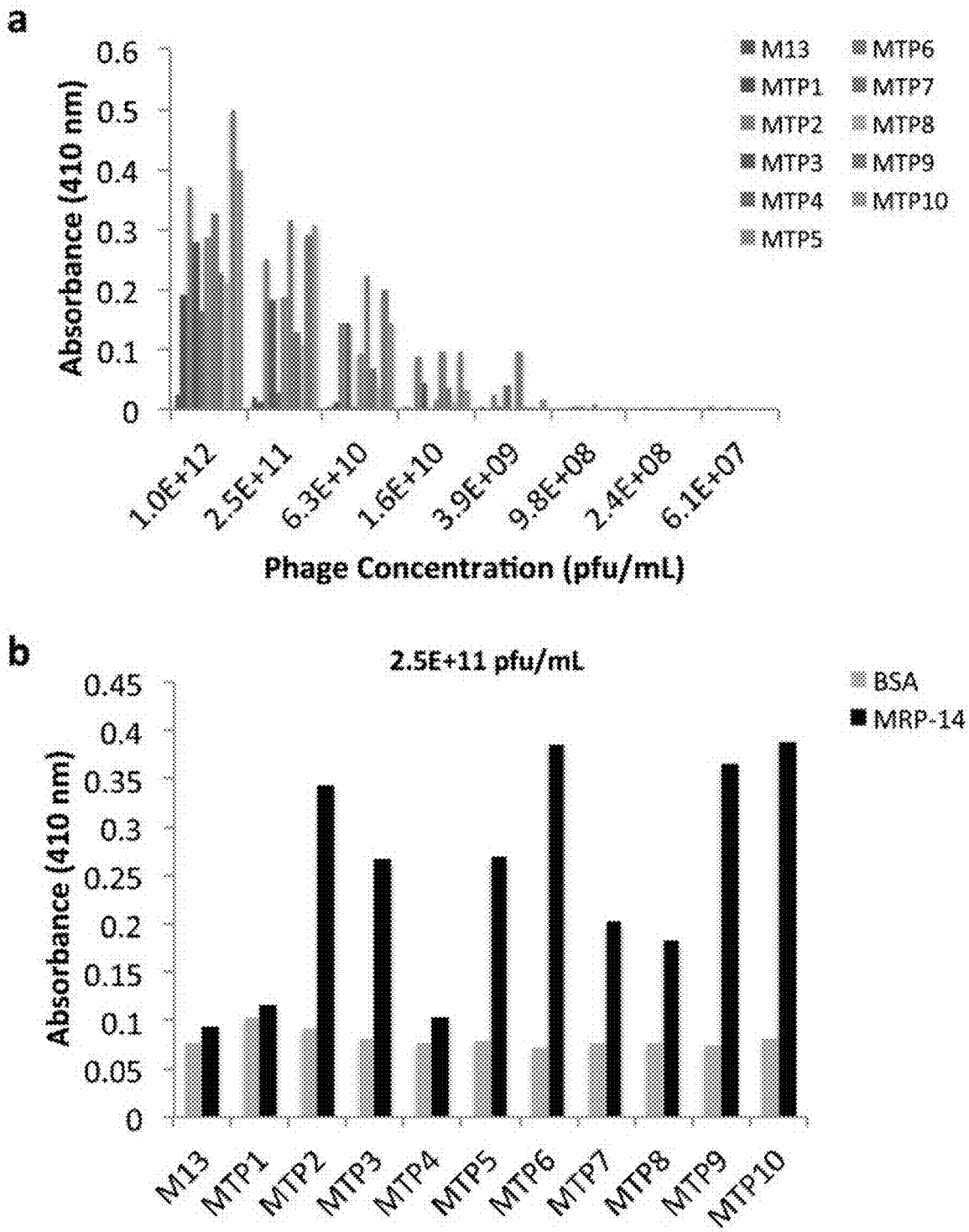
Figs. 1A-B

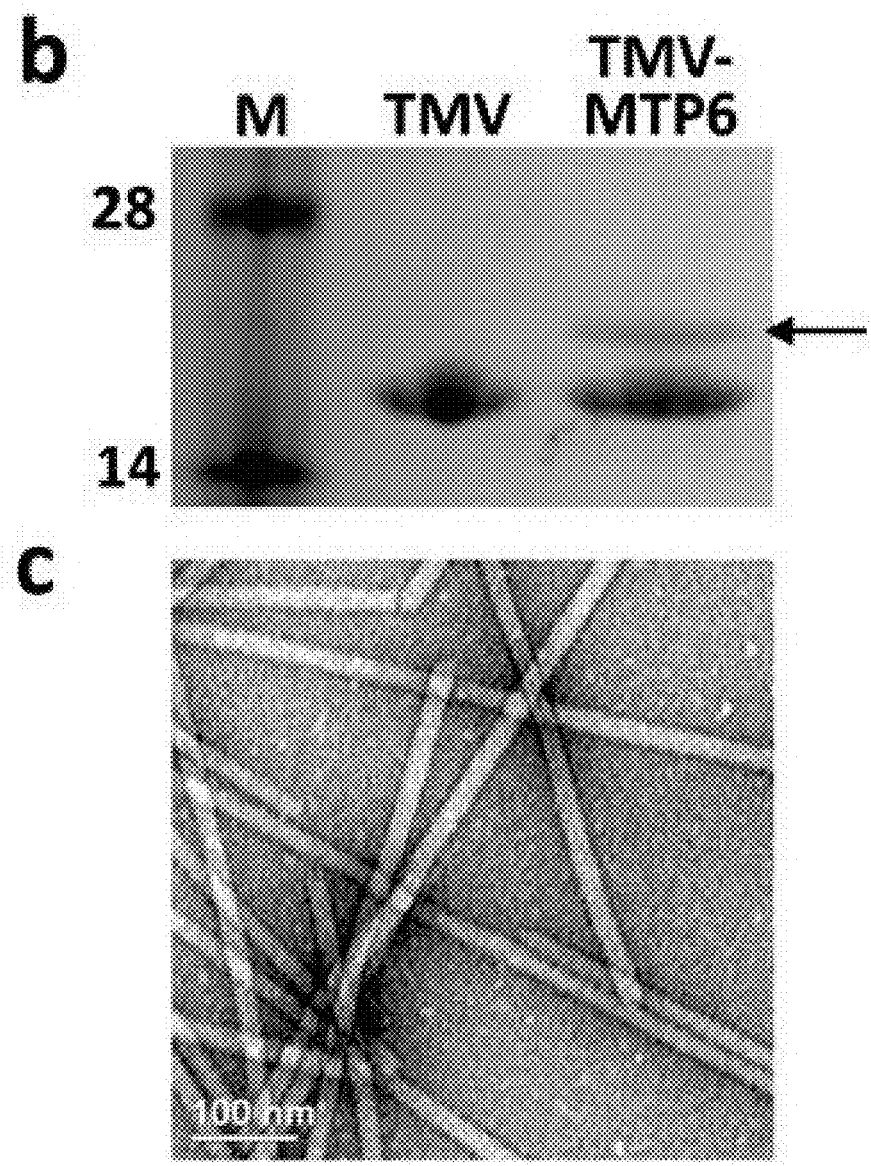
Fig. 4B-C

Fig. 6A

SEQUENCE LISTING

```
<160> NUMBER OF SEQ ID NOS: 17

<210> SEQ ID NO 1
<211> LENGTH: 7
<212> TYPE: PRT
<213> ORGANISM: Homo sapiens

<400> SEQUENCE: 1

Thr Thr Phe His His His Lys
1               5

<210> SEQ ID NO 2
<211> LENGTH: 7
<212> TYPE: PRT
<213> ORGANISM: Homo sapiens

<400> SEQUENCE: 2

Ala Ser Ser His Ile His His
1               5

<210> SEQ ID NO 3
<211> LENGTH: 7
<212> TYPE: PRT
<213> ORGANISM: Homo sapiens

<400> SEQUENCE: 3

His Asn His Met Ala Asp Pro
1               5

<210> SEQ ID NO 4
<211> LENGTH: 10
<212> TYPE: PRT
<213> ORGANISM: Homo sapiens

<400> SEQUENCE: 4

Ala Cys Lys Ala Pro Ala His His His Cys
1               5                   10

<210> SEQ ID NO 5
<211> LENGTH: 10
<212> TYPE: PRT
<213> ORGANISM: Homo sapiens

<400> SEQUENCE: 5
```

Ala Cys Asn Ser His Arg His Gly Ala Cys
1               5                   10

<210> SEQ ID NO 6
<211> LENGTH: 10
<212> TYPE: PRT
<213> ORGANISM: Homo sapiens

<400> SEQUENCE: 6

Ala Cys Asn Ser Val His Gln His His Cys
1               5                   10

<210> SEQ ID NO 7
<211> LENGTH: 10
<212> TYPE: PRT
<213> ORGANISM: Homo sapiens

<400> SEQUENCE: 7

Ala Cys Tyr Gly Lys Pro Glu His His Cys
1               5                   10

<210> SEQ ID NO 8
<211> LENGTH: 10
<212> TYPE: PRT
<213> ORGANISM: Homo sapiens

<400> SEQUENCE: 8

Ala Cys Pro His His Pro Gln Lys His Cys
1               5                   10

<210> SEQ ID NO 9
<211> LENGTH: 10
<212> TYPE: PRT
<213> ORGANISM: Homo sapiens

<400> SEQUENCE: 9

Ala Cys Pro Thr Gly Leu His His Ala Cys
1               5                   10

<210> SEQ ID NO 10
<211> LENGTH: 10
<212> TYPE: PRT
<213> ORGANISM: Homo sapiens

<400> SEQUENCE: 10

Ala Cys Arg Pro Lys Asn Asn His Ser Cys
1               5                   10

<210> SEQ ID NO 11
<211> LENGTH: 11
<212> TYPE: PRT
<213> ORGANISM: Homo sapiens

<400> SEQUENCE: 11

Met Asp Pro His Ala His Asn Gly Gly Gly Ser
1               5                   10

<210> SEQ ID NO 12
<211> LENGTH: 11
<212> TYPE: PRT
<213> ORGANISM: Homo sapiens

<400> SEQUENCE: 12

Ala Ser Ser His Ile His His Gly Gly Gly Ser
1               5                   10

```
<210> SEQ ID NO 13
<211> LENGTH: 11
<212> TYPE: PRT
<213> ORGANISM: Homo sapiens

<400> SEQUENCE: 13

His Asn His Met Ala Asp Pro Gly Gly Gly Ser
1               5                   10

<210> SEQ ID NO 14
<211> LENGTH: 14
<212> TYPE: PRT
<213> ORGANISM: Homo sapiens

<400> SEQUENCE: 14

Ala Cys Asn Ser His Arg His Gly Ala Cys Gly Gly Gly Ser
1               5                   10

<210> SEQ ID NO 15
<211> LENGTH: 14
<212> TYPE: PRT
<213> ORGANISM: Homo sapiens

<400> SEQUENCE: 15

Ala Cys Asn Ser Val His Gln His His Cys Gly Gly Gly Ser
1               5                   10

<210> SEQ ID NO 16
<211> LENGTH: 14
<212> TYPE: PRT
<213> ORGANISM: Homo sapiens

<400> SEQUENCE: 16

Ala Cys Pro Thr Gly Leu His His Ala Cys Gly Gly Gly Ser
1               5                   10

<210> SEQ ID NO 17
<211> LENGTH: 14
<212> TYPE: PRT
<213> ORGANISM: Homo sapiens

<400> SEQUENCE: 17

Ala Cys Thr Pro Lys Asn Asn His Ser Cys Gly Gly Gly Ser
1               5                   10
```

MRP-14 TARGETING PEPTIDES AND USES THEREOF

RELATED APPLICATION

This application claims priority from U.S. Provisional Application No. 62/345,939, filed Jun. 6, 2016, the subject matter of which is incorporated herein by reference in its entirety.

GOVERNMENT FUNDING

This invention was made with government support under HL129703, HL121130, HL105338 awarded by the National Institutes of Health (NIH), and CMMI 1333651 awarded by the National Science Foundation (NSF). The United States Government has certain rights in the invention

TECHNICAL FIELD

This application relates to compositions and methods for detecting, preventing, and/or treating hypercoagulation and/or thrombosis in a subject in need thereof and to methods of detecting cardiovascular disease activity in a subject.

BACKGROUND

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and prostheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules, such as collagen, or by thrombus, which is formed in the coagulation cascade.

MRP-14 is part of the S100 family comprised of small proteins (~9-14 kDa) containing two $Ca^{2+}$-binding EF hand domains. It was first identified as an acute myocardial infarction (MI) gene using transcriptional profiling of platelets from patients with acute coronary syndromes (ACS). When secreted by myeloid cells, it is predominantly found as an MRP-8/14 heterodimer in humans Studies with MRP-$14^{-/-}$ mice determined that MRP-8/14 broadly regulates vascular inflammation and promotes leukocyte recruitment in models of atherosclerosis, restenosis, and vasculitis. More recently, MRP-14 was identified as a highly expressed mediator of thrombosis found on platelets whose knockdown does not affect hemostasis. While MRP-14 deficiency is protective of thrombosis, it had no effect on hemostatic parameters such as tail bleeding time, coagulation, thrombin generation, or platelet adhesion and spreading.

SUMMARY

Embodiments describe herein relate to compositions or agents for targeting MRP-14 and to the use of the compositions or agents in diagnostic and therapeutic applications for detecting, preventing, and/or treating hypercoagulation and/or thrombosis in a subject in need thereof. The composition can include an MRP-14 targeting peptide having an amino acid sequence at least 80% identical to an amino acid sequence selected from the group consisting of SEQ ID NO: 2, SEQ ID NO: 3, SEQ ID NO: 5, SEQ ID NO: 6, SEQ ID NO: 9, and SEQ ID NO: 10. For example, the MRP-14 targeting peptide can consist of an amino acid sequence selected from the group consisting of SEQ ID NO: 2, SEQ ID NO: 3, SEQ ID NO: 5, SEQ ID NO: 6, SEQ ID NO: 9, and SEQ ID NO: 10

In some embodiments, the MRP-14 targeting peptide can be conjugated directly or indirectly to an imaging agent. The imaging agent can be detectable by at least one of gamma imaging, positron emission tomography (PET) imaging, computer tomography (CT) imaging, magnetic resonance imaging, near infrared imaging, or fluorescent imaging. The imaging agent can include, for example, at least one of radio labels, contrast agents, fluorescent dyes, chemiluminescent agents, colorimetric labels, and magnetic labels.

In other embodiments, the MRP-14 targeting peptide can be conjugated to and/or linked to a nanocarrier. In some embodiments, the nanocarrier can be a plant virus particle or virus like particle. In some embodiments, the plant virus particle or virus like particle is a rod-shaped virus particle, such as a tobacco mosaic virus (TMV) or tobacco mosaic virus like particle.

Other embodiments described herein, relate to a method of detecting thrombus formation in a subject in need thereof. The method includes administering to the subject a molecular probe that includes an MRP-14 targeting peptide. The MRP-14 targeting peptide can have an amino acid sequence at least 80% identical to an amino acid sequence selected from the group consisting of SEQ ID NO: 2, SEQ ID NO: 3, SEQ ID NO: 5, SEQ ID NO: 6, SEQ ID NO: 9, and SEQ ID NO: 10. The molecular probes bound to MRP-14 in the subject's vasculature can then be detected to determine the location, and/or distribution of thrombus formation in the subject.

In some embodiments of the method, the MRP-14 targeting peptide can consist of an amino acid sequence selected from the group consisting of SEQ ID NO: 2, SEQ ID NO: 3, SEQ ID NO: 5, SEQ ID NO: 6, SEQ ID NO: 9, and SEQ ID NO: 10.

In other embodiments, the MRP-14 targeting peptide can be conjugated directly or indirectly to an imaging agent. The imaging agent can be detectable by at least one of gamma imaging, positron emission tomography (PET) imaging, computer tomography (CT) imaging, magnetic resonance imaging, near infrared imaging, or fluorescent imaging. The imaging agent can include, for example, at least one of radio labels, contrast agents, fluorescent dyes, chemiluminescent agents, colorimetric labels, and magnetic labels.

In still other embodiments, the MRP-14 targeting peptide and imaging agent can be conjugated and/or linked to a nanocarrier. In some embodiments, the nanocarrier can be a plant virus particle or virus like particle. In some embodiments, the plant virus particle or virus like particle is a rod-shaped virus particle, such as a tobacco mosaic virus (TMV) or tobacco mosaic virus like particle.

In some embodiments, the subject can be prone to or suffer from a cardiovascular disease. The cardiovascular disease can be selected from the group consisting of acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, and thrombotic and restenotic complications following invasive procedures resulting from angioplasty, carotid endarterectomy, post CABG (coronary artery bypass graft) surgery, vascular graft surgery, stent placements and insertion of endovascular devices and prostheses.

Still other embodiments relate to a method of delivering a therapeutic and/or imaging agent to thrombus in a subject. The method can be administering to the subject a composition. The composition can include an MRP-14 targeting peptide and a therapeutic agent and/or imaging agent conjugated or linked to the MRP-14 targeting peptide. The MRP-14 targeting peptide can have an amino acid sequence at least 80% identical to an amino acid sequence selected from the group consisting of SEQ ID NO: 2, SEQ ID NO: 3, SEQ ID NO: 5, SEQ ID NO: 6, SEQ ID NO: 9, and SEQ ID NO: 10.

In still other embodiments, the MRP-14 targeting peptide and imaging agent and/or therapeutic agent can be conjugated to and/or linked to a nanocarrier. In some embodiments, the nanocarrier can be a plant virus particle or virus like particle. In some embodiments, the plant virus particle or virus like particle is a rod-shaped virus particle, such as a tobacco mosaic virus (TMV) or tobacco mosaic virus like particle.

In some embodiments, the composition can inhibit thrombosis in the subject without inhibiting hemostasis. The composition can be administered intravenously or subcutaneously to the subject.

Other embodiments described herein relate to a composition comprising a plant virus particle or virus like particle and a plurality of MRP-14 targeting peptides conjugated to the plant virus particle or virus like particle. The MRP-14 targeting peptide can have an amino acid sequence at least 80% identical to an amino acid sequence selected from the group consisting of SEQ ID NO: 2, SEQ ID NO: 3, SEQ ID NO: 5, SEQ ID NO: 6, SEQ ID NO: 9, and SEQ ID NO: 10.

In some embodiments, the composition can further include at least one imaging agent or therapeutic agent conjugated to the plant virus particle or virus like particle. In some embodiments, the plant virus particle or virus like particle is a rod-shaped plant virus particle or virus like particle.

In other embodiments, at least 200 MRP-14 targeting peptides can be conjugated to the plant virus particle or virus like particle.

BRIEF DESCRIPTION OF THE DRAWINGS

FIGS. 1(A-B) illustrate graphs showing peptide identification and ELISA characterization. A) Phage ELISA to determine binding to MRP-14 using fourfold serial dilutions of phages from a starting concentration of $10^{12}$ pfu/mL to a final concentration of $6 \times 10^7$ pfu/mL. Absorbance values are after background subtraction. B) For simplicity, values of background binding to BSA and specific binding to MRP-14 are shown for a single dilution ($2.5 \times 10^{11}$ pfu/mL) to more easily compare the affinity of the various displayed peptides.

DETAILED DESCRIPTION

Figure 2A:
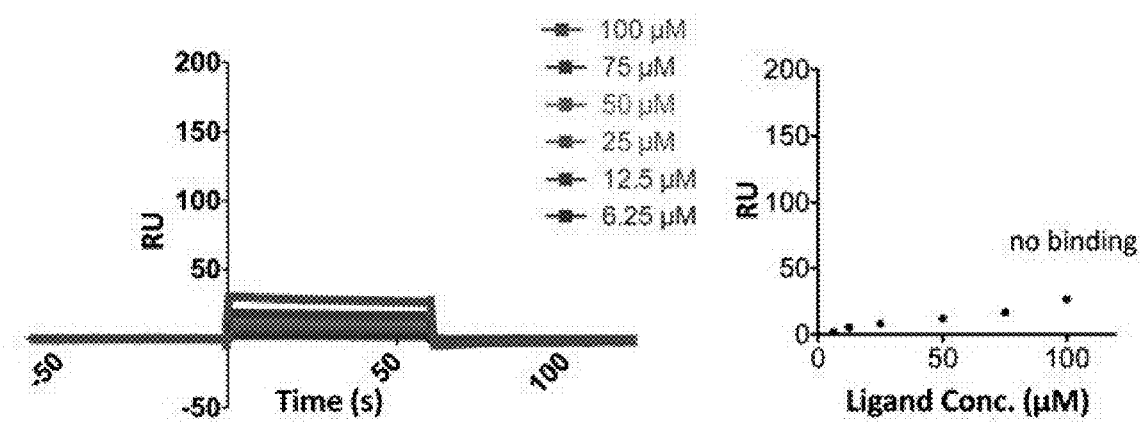
FIGS. 2(A-H) illustrate plots showing SPR analysis of peptides SPR sensorgram data for peptide binding to immobilized MRP-14 and determination of the dissociation constant using a rectangular hyperbola fit of the saturation binding curve are shown as pairs for all peptides, including a scrambled control and azide-functionalized MTP6. All data shown are one of two similar experiments, and analysis was performed with Prism software. The scrambled peptide experienced low non-specific binding and the data could not be fit. MTP9 had a unique profile compared to the others and was fit using a kinetic curve rather than an equilibrium affinity binding curve.
Figure 2B:
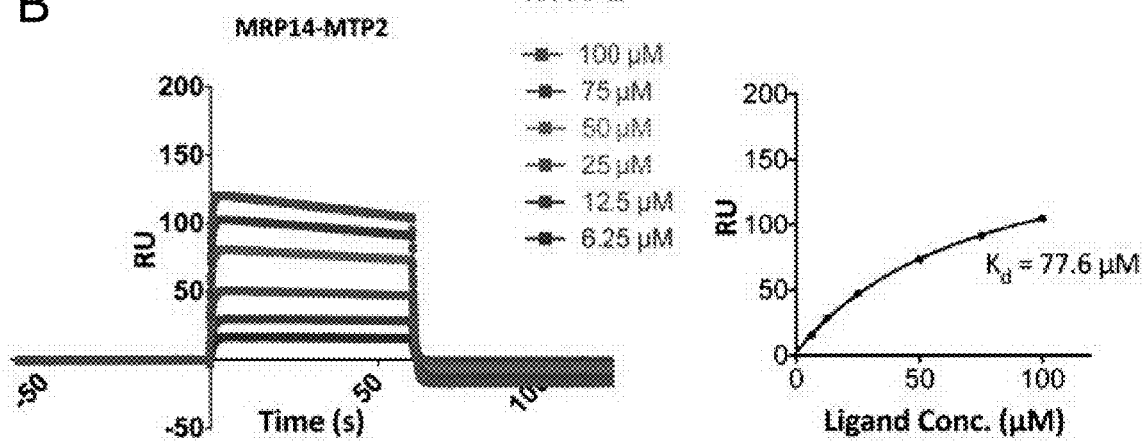
Figure 2C:
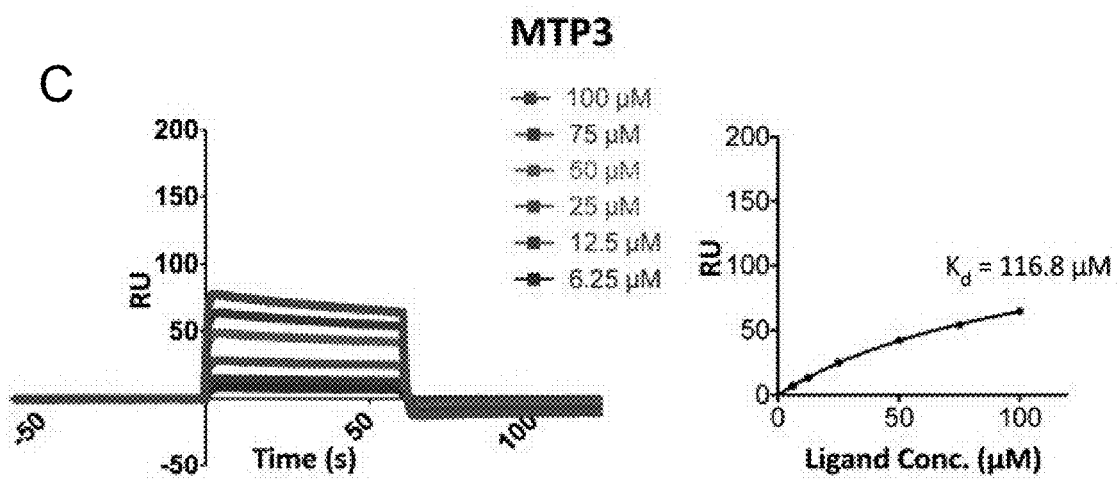
Figure 2D:
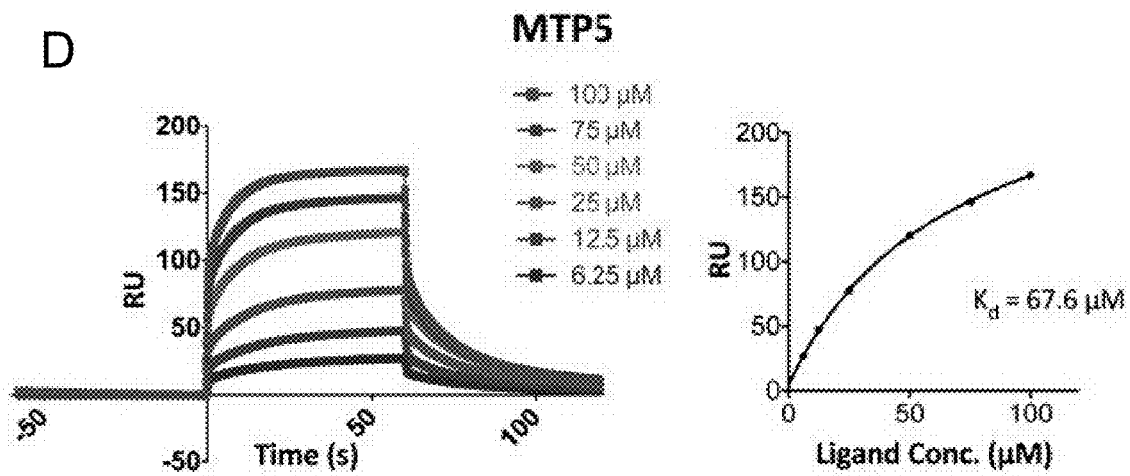
Figure 2E:
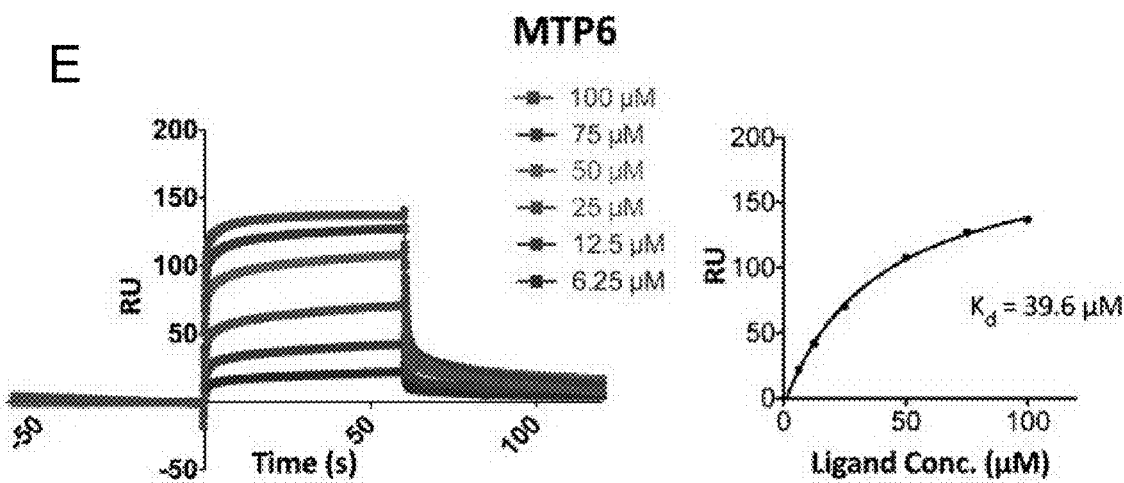
Figure 2F:
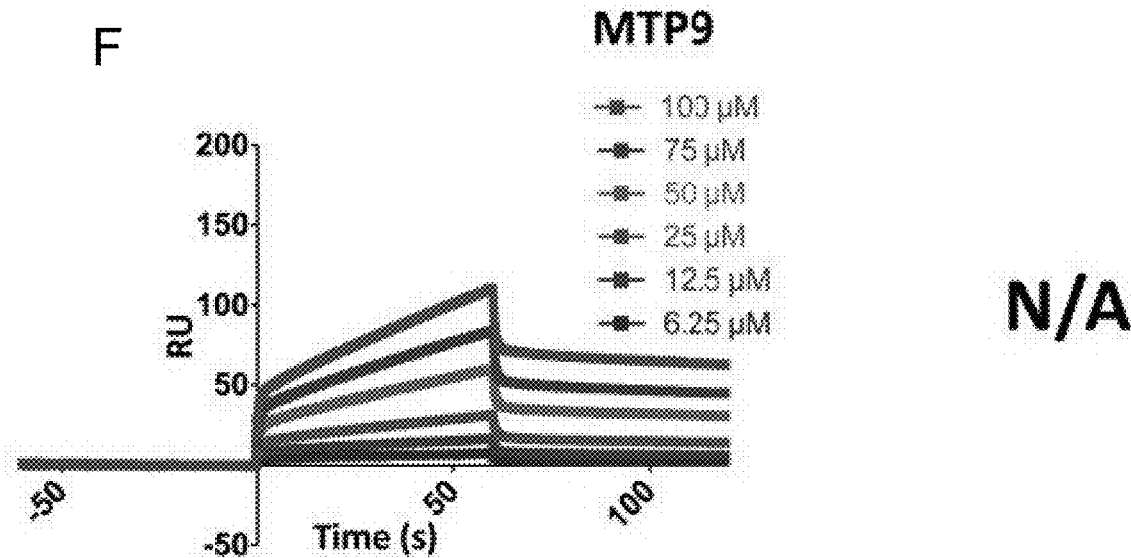
Figure 2G:
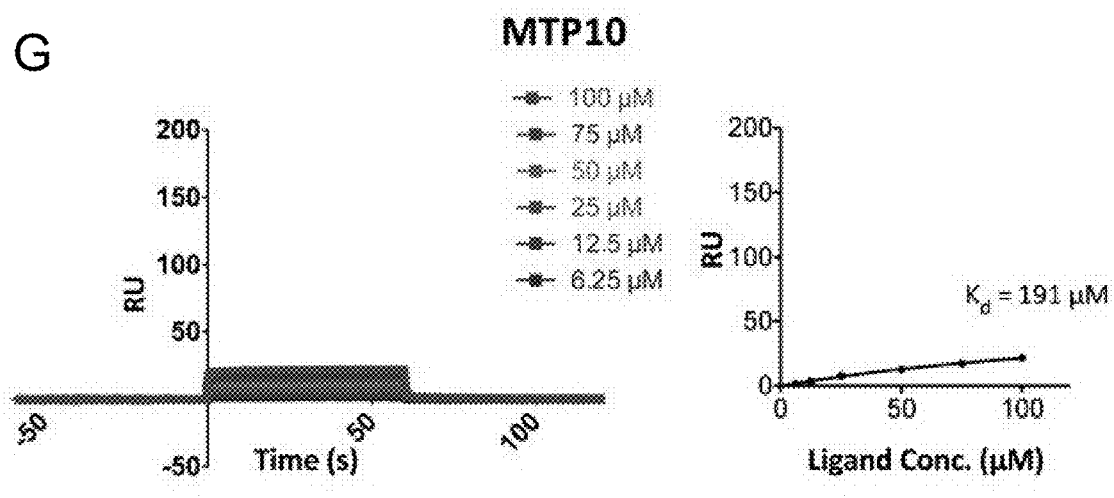
Figure 2H:
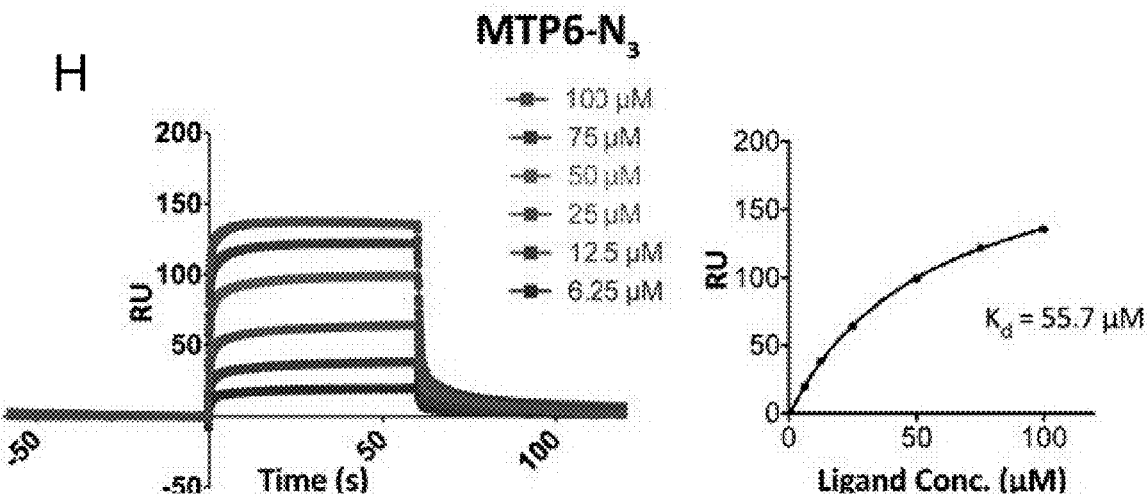

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, Genes V, Oxford University Press: New York, 1994.

The term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "agent" is used herein to denote a chemical compound, a mixture of chemical compounds, a biological macromolecule, or an extract made from biological materials.

The term "imaging agent" can refer to a biological or chemical moiety capable being linked and/or conjugated directly or indirectly to targeting peptides described herein and that may be used to detect, image, and/or monitor the presence and/or progression of a cell cycle, cell function/physiology, condition, pathological disorder and/or disease.

The term "isolated" refers to material that is removed from its original environment. A cell is isolated if it is separated from some or all of the components that normally accompany it in its native state. For example, an "isolated population of cells," an "isolated source of cells," or "isolated platelets" and the like, as used herein, refer to in vitro or ex vivo separation of one or more cells from their natural cellular environment, and from association with other components of the tissue or blood, i.e., it is not significantly associated with in vivo substances.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The terms "patient", "subject", "mammalian host", and the like are used interchangeably herein, and refer to mammals, including human and veterinary subjects.

The term "polypeptide" or "peptide" is meant to refer to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides described herein will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis.

The phrases "parenteral administration" and "administered parenterally" refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The terms "prevent", "preventing", "prevention", "prophylactic treatment" and the like are meant to refer to reducing the probability of developing a disorder or condition in a subject, who does not have, but is at risk of or susceptible to developing a disorder or condition. Prevention and the like do not mean preventing a subject from ever getting the specific disease or disorder. Prevention may require the administration of multiple doses. Prevention can include the prevention of a recurrence of a disease in a subject for whom all disease symptoms were eliminated, or prevention of recurrence in a relapsing—remitting disease.

The term "soluble" as used herein is meant that a polypeptide, such as a fusion protein, that is not readily sedimented under low G-force centrifugation (e.g., less than about 30,000 revolutions per minute in a standard centrifuge) from an aqueous buffer, e.g., cell media. Further, the polypeptide is soluble if it remains in aqueous solution at a temperature greater than about 5-37° C. and at or near neutral pH in the presence of low or no concentration of an anionic or non-ionic detergent. Under these conditions, a soluble polypeptide will often have a low sedimentation value, e.g., less than about 10 to 50 svedberg units.

Aqueous solutions referenced herein typically have a buffering compound to establish pH, typically within a pH range of about 5-9, and an ionic strength range between about 2 mM and 500 mM. Sometimes a protease inhibitor or mild non-ionic detergent is added.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

"More than one" is understood as 2, 3, 4, 5, 6, 7, 8, 9, 10, 11, 12, 13, 14, 15, 16, 17, 18, 19, 20, 25, 30, 40, 50, 100, etc., or any value there between. "At least" a specific value, is understood to be that value and all values greater than that value.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Embodiments describe herein relate to compositions or agents for targeting MRP-14 and to the use of the compositions or agents in diagnostic and therapeutic applications for detecting, preventing, and/or treating hypercoagulation and/or thrombosis in a subject in need thereof. As described in the Example, we identified peptides specific fro MRP-14 and were able to conjugate the peptides to a nanoparticle carrier. The MRP-14 targeting peptides conjugated to the nanocarrier showed no aggregation and stimulation of thrombosis and were able to target thrombosis in an ex vivo flow model as well as in vivo photochemical injury mouse model of thrombosis.

The MRP-14 targeting peptides can be used in diagnostic, therapeutic, and/or theranostic applications to deliver therapeutic agents and/or imaging agents to sites of thrombus formation or thrombosis in a subject as well as selectively target thrombosis of a subject upon systemic administration (e.g., intravenous, intravascular, intraarterial infusion) of the compositions comprising the targeting peptides to the subject.

In some embodiments, the MRP-14 targeting peptide can include, consist essentially of, or consist of about 7 to about 15 amino acids and have an amino acid sequence that is substantially identical to about 7 to about 15 consecutive amino acids of an amino acid sequence selected from the group consisting of SEQ ID NO: 2, SEQ ID NO: 3, SEQ ID NO: 5, SEQ ID NO: 6, SEQ ID NO: 9, and SEQ ID NO: 10. By substantially identical, it is meant the targeting peptide has at least about 80%, about 90%, about 95%, about 96%, about 97%, about 98%, about 99% or about 100% sequence identity with an amino acid sequence selected from the group consisting of SEQ ID NO: 2, SEQ ID NO: 3, SEQ ID NO: 5, SEQ ID NO: 6, SEQ ID NO: 9, and SEQ ID NO: 10.

The MRP-14 targeting peptide can be in any of a variety of forms of polypeptide derivatives and include, for example, amides, conjugates with proteins, cyclized polypeptides, polymerized polypeptides, analogs, fragments, chemically modified polypeptides, and the like derivatives.

The term "analog" includes any peptide having an amino acid residue sequence substantially identical to a sequence specifically shown herein in which one or more residues have been conservatively substituted with a functionally similar residue and that specifically binds to and/or complexes with MRP-14 and/or MRP-8/14. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue, such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

Additional residues may also be added at either terminus of a polypeptide for the purpose of providing a "linker" by which the polypeptides can be conveniently linked and/or affixed to other polypeptides, proteins, imaging agents, therapeutic agents, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-NH$_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the MRP-14 targeting peptide to other polypeptides, proteins, and/or molecules, such as imaging agents, therapeutic agents, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

The MRP-14 targeting peptides can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production, and the like. A summary of the many techniques available can be found in, for example: Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

It will be appreciated that the MRP-14 targeting peptides described herein can be used as a starting point to develop higher affinity small molecules or peptides with similar ligand binding capabilities. The development and screening of small molecules from pharmacophores of the peptides using, for example, in silico screening, can be readily performed, and the binding affinity of such identified molecules can be readily screened against the targeting peptides using assays described herein to select small molecule agents.

In some embodiments, the MRP-14 targeting peptide can be directly or indirectly bound to, conjugated to, and/or linked to an imaging agent (or detectable moieties) therapeutic agent, and/or bioactive agent.

Imaging agents can include any substance that may be used for imaging or detecting a region of interest (ROI) in a subject and/or diagnosing the presence or absence of a disease or diseased tissue in a subject. The imaging agent can be selected such that it generates a signal, which can be measured and whose intensity is related (preferably proportional) to the distribution of the imaging agent and thrombus formation in the subject. Methods for labeling biological molecules, such as polypeptides are well-known in the art.

Any of a wide variety of imagings agents can be used with the targeting peptides described herein. Examples of imaging agents include, but are not limited to: radiolabels, radionuclides, fluorescent dyes, chemiluminescent agents, colorimetric labels, and magnetic labels.

In some embodiments, a molecular probe including the MRP-14 targeting peptide described herein and an imaging agent may be used in conjunction with non-invasive imaging techniques for in vivo imaging, such as magnetic resonance spectroscopy (MRS) or imaging (MRI), or gamma imaging, such as positron emission tomography (PET) or single-photon emission computed tomography (SPECT). The term "in vivo imaging" refers to any method, which permits the detection of a labeled molecular probe, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

For purposes of in vivo imaging, the type of detection instrument available is a major factor in selecting a given imaging agent. For instance, the type of instrument used will guide the selection of the stable isotope. The half-life should be long enough so that it is still detectable at the time of maximum uptake by the target, but short enough so that the host does not sustain deleterious effects.

In one example, the imaging agent can include a radiolabel, that is coupled (e.g., attached or complexed) with the targeting peptide using general organic chemistry techniques. The detectable moiety can also include radiolabels, such as $^{123}$I, $^{131}$I, $^{125}$I, $^{18}$F, $^{11}$C, $^{75}$Br, $^{76}$Br, $^{124}$I, $^{13}$N, $^{64}$Cu, $^{32}$P, $^{35}$S, for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The imaging agent can also include $^{123}$I for SPECT. The $^{123}$I can be coupled to the imaging agent can by any of several techniques known to the art. See, e.g., Kulkarni, Int. J. Rad. Appl. & Inst. (Part B) 18: 647 (1991), the contents of which are hereby incorporated by reference. In addition, imaging agent can include any radioactive iodine isotope, such as, but not limited to $^{131}$I, $^{125}$I, or $^{123}$I. The radioactive iodine isotopes can be coupled to the imaging agent by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl derivative which then can be converted to the iodo compound by several methods well known to the art.

The imaging agent can further include known metal radiolabels, such as Technetium-99m ($^{99m}$Tc), $^{153}$Gd, 111In, $^{67}$Ga, $^{201}$Tl, $^{68}$Ga, $^{82}$Rb, $^{64}$Cu, $^{90}$Y, $^{188}$Rh T(tritium), $^{153}$Sm, $^{89}$Sr, and $^{211}$At. Modification of the targeting peptide to introduce ligands that bind such metal ions can be effected without undue experimentation by one of ordinary skill in the radiolabeling art. The metal radiolabeled molecular probes can then be used to detect thrombus formation in the subject. Preparing radiolabeled derivatives of Tc99m is well known in the art. See, for example, Zhuang et al., "Neutral and stereospecific Tc-99m complexes: [99mTc]N-benzyl-3, 4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

Fluorescent labeling agents or infrared agents include those known to the art, many of which are commonly commercially available, for example, fluorophores, such as ALEXA 350, PACIFIC BLUE, MARINA BLUE, ACRIDINE, EDANS, COUMARIN, BODIPY 493/503, CY2, BODIPY FL-X, DANSYL, ALEXA 488, FAM, OREGON GREEN, RHODAMINE GREEN-X, TET, ALEXA 430, CAL GOLD™, BODIPY R6G-X, JOE, ALEXA 532, VIC, HEX, CAL ORANGE™, ALEXA 555, BODIPY 564/570, BODIPY TMR-X, QUASAR™ 570, ALEXA 546, TAMRA, RHODAMINE RED-X, BODIPY 581/591, CY3.5, CYS, CY5.5, ROX, ALEXA 568, CAL RED, BODIPY TR-X, ALEXA 594, BODIPY 630/650-X, PULSAR 650, BODIPY 630/665-X, ALEXA 647, IR800, and QUASAR 670. Fluorescent labeling agents can include other known fluorophores, or proteins known to the art, for example, green fluorescent protein. The disclosed targeting peptides can be coupled to the fluorescent labeling agents, administered to a subject or a sample, and the subject/sample examined by fluorescence spectroscopy or imaging to detect the labeled compound.

Quantum dots, e.g., semiconductor particles, can be employed as described in Gao, et al "In vivo cancer targeting and imaging with semiconductor quantum dots", Nature Biotechnology, 22, (8), 2004, 969-976, the entire teachings of which are incorporated herein by reference. The disclosed targeting peptides can be coupled to the quantum dots, administered to a subject or a sample, and the subject/sample examined by fluorescence spectroscopy or imaging to detect the labeled compound.

Numerous magnetic resonance imaging (MRI) contrast agents are known to the art, for example, positive contrast agents and negative contrast agents. The disclosed targeting peptides can be coupled to the MRI agents, administered to a subject or a sample, and the subject/sample examined by MRI or imaging to detect the labeled compound. Positive contrast agents (typically appearing predominantly bright on MRI) can include typically small molecular weight organic compounds that chelate or contain an active element having unpaired outer shell electron spins, e.g., gadolinium, manganese, iron oxide, or the like. Typical contrast agents include gadolinium(III)chelates, such as gadopentetate dimeglumine, gadoteridol, gadoterate meglumine, mangafodipir trisodium, gadodiamide, and others known to the art. Negative contrast agents (typically appearing predominantly dark on MRI) can include small particulate aggregates comprised of superparamagnetic materials, for example, particles of superparamagnetic iron oxide (SPIO). Negative contrast agents can also include compounds that lack the hydrogen atoms associated with the signal in MRI imaging, for example, perfluorocarbons (perfluorochemicals).

In other embodiments, therapeutic agents or bioactive conjugated to and/or linked to the targeting peptides described herein can include any substance capable of exerting a biological or therapeutic effect in vitro and/or in vivo. Therapeutic agents can also include any therapeutic or prophylactic agent used in the treatment (including the prevention, diagnosis, alleviation, or cure) of a malady, affliction, condition, disease or injury in a subject. Examples of therapeutic agents include, but are not limited to thrombolytic, anti-thrombosis, and anti-proliferative agents. The therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

In some embodiments, the therapeutic agent can be a thrombolytic agent that is conjugated to and/or linked to the targeting peptide. Thrombolytic agents are used to dissolve blood clots in a procedure termed thrombolysis and can limit the damage caused by the blockage or occlusion of a blood vessel. Thrombolytic agents can include analogs of tissue plasminogen activator (tPA), the protein that normally activates plasmin and recombinant tissue plasminogen activators (r-tPAs) include alteplase, reteplase, and tenecteplase (sold under the trade name TNKase) and desmoteplase. Additional thrombolytic agents include anistreplase (sold under the trade name EMINASE), streptokinase (sold under the trade names KABIKINASE, STREPTASE), and urokinase (sold under the trade name ABBOKINASE).

In some embodiments, the therapeutic agent can be an anti-thrombotic agent that is directly or indirectly conjugated to and/or linked to the MRP-14 targeting peptides described herein. Antithrombotic agents can include anticoagulants and antiplatelet agents.

Anticoagulants slow down clotting, thereby reducing fibrin formation and preventing clots from forming and growing. Anticoagulants include coumarins (vitamin K antagonists) such as coumadin. Anticoagulants also include but are not limited to heparin, heparin derivatives and direct thrombin inhibitors including the bivalent drugs hirudin, lepirudin, and bivalirudin and the monovalent drugs argatroban and dabigatran.

Antiplatelet agents prevent platelets from clumping and also prevent clots from forming and growing. Antiplatelet agents can include but are not limited to aspirin and clopidogrel (sold under the trade name PLAVIX).

In some embodiments, one or more of the MRP-14 targeting peptides and optionally an imaging agent and/or therapeutic agent can be bound to, conjugated to, and/or decorated on a surface of a nanocarrier, such as a nanoparticle, to provide a composition or nanoparticle construct with enhanced specificity and affinity to MRP-14 compared to MRP-14 targeting peptides used alone. The nanoparticle can provide a platform for displaying a plurality of MRP-14 targeting peptides as well for conjugating and/or delivering imaging agents and/or therapeutic agents to sites of thrombosis.

In some embodiments, the nanoparticles can have a maximum length or diameter of about 100 nm to about 10 µm. In general, the nanoparticle construct can have dimensions small enough to allow a composition comprising such constructs to be systemically administered to a subject and targeted to sites of thrombus formation in the vasculature of the subject.

The nanoparticles of the composition may be uniform (e.g., being about the same size) or of variable size. Particles may be any shape (e.g., spherical or rod shaped), but are preferably made of regularly shaped material (e.g., rod shaped). Other geometries can include substantially spherical, circular, triangle, quasi-triangle, square, rectangular, hexagonal, oval, elliptical, rectangular with semi-circles or triangles and the like. Selection of suitable materials and geometries are known in the art.

In some embodiments, the nanoparticles can be based on plant virus particles and include plant virus nanoparticles and/or plant virus like particles. Plant virus particles preferably grow in plants, and have the advantages of being readily cultivated, and are unlikely to cause infection when used in vivo in a subject. Plant virus particles are categorized based on their source and structure. In various embodiments, virus particles having an icosahedral, filamentous, or rod-shaped structure can be used. The virus particles can be non-enveloped virus particles. Examples of icosahedral plant viruses include cowpea mosaic virus, brome mosaic virus, cowpea chlorotic mottle virus, etc. Advantageously, filamentous and/or rod-shaped plant virus particles can be used as they have been shown to possess greater thrombosis targeting properties and have a greater capacity for drifting laterally toward the vessel wall and enhanced vascular interaction upon encountering the disease site due to having greater surface areas with better presentations of targeting peptides.

A filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm.

In some embodiments, the filamentous plant virus belongs to a specific virus family, genus, or species. For example, in some embodiments, the filamentous plant virus belongs to the Alphaflexiviridae family. The Alphaflexiviridae family includes the genus *Allexivirus, Botrexvirus, Lolavirus, Mandarivirus, Potexvirus*, and *Sclerodamavirus*. In some embodiments, the filamentous plant virus belongs to the genus *Potexvirus*. In further embodiments, the filamentous plant virus belongs to the Potato Virus X species.

In other embodiments, the nanoparticle can be based on a rod-shaped plant virus or virus like particle. A rod-shaped plant virus is a virus that primarily infects plants, is non-enveloped, and is shaped as a rigid helical rod with a helical symmetry. Rod-shaped plant viruses also include a central hollow canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, the rod-shaped plant virus belongs to the Virgaviridae family. The Virgaviridae family includes the genus *Furovirus, Hordevirus, Pecluvirus, Pomovirus, Tobamovirus*, and *Tobravirus*. In some embodiments, the rod-shaped plant virus belongs to the genus *Tobamovirus*. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are about 300 nm in length and about 18 nm in diameter. Negatively stained electron micro-photographs show a distinct inner channel of about 4 nm.

In other embodiments, the plant virus or virus like particle is an icosahedral plant virus or virus like particle. Examples of icosahedral plant viruses include the virus families Geminiviridae, Luteoviridae, Bromoviridae, Phycodnaviridae, and Picornaviridae. In some embodiments, the icosahedral plan virus is from the family Picornaviridae. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily Examples of viruses from the Comovirinae subfamily include Cowpea mosaic virus, Broad bean wilt virus 1, and Tobacco ringspot virus. In a further embodiment, the virus particles are from the Genus comovirus. An example of a comovirus is the cowpea mosaic virus particles.

The MRP-14 targeting peptides described herein and optionally the imaging agents and/or therapeutic agents can be linked to and/or conjugated to the plant viral nanoparticles or virus like particles either directly or indirectly (e.g., via a linker). In some embodiments, the MRP-14 targeting peptides and optionally the imaging agents and/or therapeutic agents are directly attached to a functional group capable of reacting with the MRP-14 targeting peptides and optionally the imaging agents and/or therapeutic agents. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g., alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

Alternatively, a peptide or chemical linker or linker group can be used. A linker group can serve to increase the chemical reactivity of a substituent on either the MRP-14 targeting peptides and optionally the imaging agents and/or therapeutic agents or the virus particle, and thus increase the coupling efficiency. Examples of linkage chemistries include maleimidyl linkers, which can be used to link to thiol groups, isothiocyanate and succinimidyl (e.g., N-hydroxy-succinimidyl (NHS)) linkers, which can link to free amine groups, diazonium which can be used to link to phenol, and amines, which can be used to link with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and heterofunctional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, more than one type of MRP-14 targeting peptide and optionally imaging agent and/or therapeutic agent can be attached to a plant virus particle. In some embodiments, differences in the linking sites available on the outside surface (i.e., exterior) and inside channel (i.e., interior) of the virus particle can be used to provide a virus particle with different imaging agents and/or therapeutic agents on the inside and outside of the virus particle. For example, the virus particle or virus like particle can have a plurality of MRP-14 targeting peptide on the outside of the particle, first imaging agent on the insider of the particle, and a second, different imaging agent on the outside of the virus particle or virus like particle. The different linking sites allow different linking chemistries to be used for the interior and exterior portions of the virus particle or virus like particle.

The number of MRP-14 targeting peptides and optionally imaging agents and/or therapeutic agents that can be loaded onto the virus particle or virus like particle depends on the number of attachment sites available and the chemistries employed to link the agents to the virus particle or virus like particle. In some embodiments, each virus particle or virus like particle is loaded with about 10, 25, 50, 100, 200, 300, 400, 500, or more MRP-14 targeting peptides and optionally imaging agents and/or therapeutic agents molecules.

In some embodiments, the MRP-14 targeting peptides and optionally imaging agents, therapeutic agents, and/or nanoparticles described herein can be provided in a pharmaceutical composition for administration to a subject in need thereof. The pharmaceutical compositions can include a pharmaceutically effective amount of a therapeutic agents described above and a pharmaceutically acceptable diluent or carrier.

The term "pharmaceutically acceptable carrier", "diluents", "adjuvant" and "physiologically acceptable vehicle" and the like are to be understood as referring to an acceptable carrier or adjuvant that may be administered to a patient, together with an agent of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In some embodiments, the compositions or pharmaceutical compositions comprising the targeting peptides described herein can be used in methods of detecting and/or treating disease states in mammals which have disorders related to coagulation, such as in the detection, treatment, and/or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries and/or vasculature. Further, these compositions are useful for the detection, treatment, and/or prophylaxis of those diseases which involve a number of thrombotic or thromboembolic events.

The term, "thrombotic or thromboembolic event," includes any disorder that involves a blockage or partial blockage of an artery or vein with a thrombosis or thromboembolism, all of which can be treated by the compositions described herein. A "thrombosis" is the formation of a clot (or thrombus) inside a blood vessel that can obstruct the flow of blood through the circulatory system. A "thromboembolism" involves formation in a blood vessel of a clot (thrombus) that breaks loose and is carried by the blood stream to lodge in another vessel area. The clot may lodge in a vessel in the lungs (pulmonary embolism), brain (stroke), gastrointestinal tract, kidneys, or leg. Thromboembolism is an important cause of morbidity (disease) and mortality (death), especially in adults.

A thrombotic or thromboembolic event occurs when a clot forms and lodges within a blood vessel. The clot may fully or partially block the blood vessel causing a thrombotic disorder such as a heart attack or stroke. Examples of thrombotic or thromboembolic events include thrombotic disorders such as acute myocardial infarction, unstable angina, ischemic stroke, acute coronary syndrome, pulmonary embolism, transient ischemic attack, thrombosis (e.g., deep vein thrombosis, thrombotic occlusion and re-occlusion and peripheral vascular thrombosis) and thromboembolism. A thrombotic or thromboembolic event also includes first or subsequent thrombotic stroke, acute myocardial infarction, which occurs subsequent to a coronary intervention procedure, or thrombolytic therapy.

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

In some embodiments, the compositions described herein are useful in detecting and/or treating thromboembolic stroke, ischemic or hemorrhagic stroke, systemic embolism, stroke prevention in atrial fibrillation (SPAF), non-valvular atrial fibrillation, venous thromboembolism (VTE), prevention of VTE in knee or hip surgery, prevention of VTE in acute medically ill patients, and secondary prevention in acute coronary syndrome (ACS).

In some embodiments, the compositions are for the detection and/or treatment of embolic stroke, thrombotic stroke, venous thrombosis, deep venous thrombosis, acute coronary syndrome, or myocardial infarction.

In some embodiments, the compositions are for the detection and/or prevention of stroke in atrial fibrillation patients; prevention of thrombosis in medically ill patients; prevention and treatment of deep vein thrombosis; prevention of arterial thrombosis in acute coronary syndrome patients; and/or secondary prevention of myocardial infarction, stroke or other thrombotic events in patients who have had a prior event.

In some embodiments, the patient has atrial fibrillation. In some embodiments, the patient is a patient with non-valvular atrial fibrillation. In some embodiments, the patient has atrial flutter.

The compositions described herein can be administered e.g., intravenously, parenterally, orally, subcutaneously, intramuscularly, transdermally (for example using an iontophoretic patch), intraocularly, intranasally, by inhalation, by implant, by suppository, or by other routes known to those skilled in the medical arts, taking into account the particular properties of the composition being administered and the particular therapy.

In one embodiment, the composition comprising the MRP-14 targeting peptide may be administered on an ongoing basis to detect, treat, and/or prevent angina, myocardial infarction, stroke, pulmonary embolism, transient ischemic attack, coronary ischemic syndrome, Syndrome X, heart failure, diabetes, disorders in which a narrowing of at least one coronary artery occurs, thrombosis including catheter thrombosis, deep vein thrombosis, arterial vessel thrombosis, and peripheral vascular thrombosis, or thrombotic occlusion and re-occlusion, including re-occlusion subsequent to a coronary intervention procedure, or in connection with heart surgery or vascular surgery.

Diagnostically and/or therapeutically effective amounts of the MRP-14 targeting peptides and optionally imaging agents and/or therapeutic agents are suitable for use in the compositions and methods described herein. The dosage regimen is selected in accordance with a variety of factors including type, species, age, weight, sex and medical condition of the patient; the severity of the condition to be treated; the route of administration; the renal and hepatic function of the patient; and the particular compound or salt or ester thereof employed.

Other embodiments described herein relate to a method of determining, predicting, or prognosticating whether a subject has an increased risk of thrombosis and/or cardiovascular disease activity by detecting the location and/or distribution of MRP-14 in the vasculature of the subject. The major cause of acute coronary syndromes, including myocardial infarction and unstable angina, is plaque rupture and thrombosis. These ischemic events are typically precipitous without warning symptoms. Elevated MRP-14 levels, including platelet MRP-14 levels, have found to be one of the strongest predictors of myocardial infarction in a subject with coronary artery disease as well as serve as an early and sensitive marker of myocardial necrosis. In some embodiments, the subjects risk of hypercoagulation, thrombosis, and/or cardiovascular disease activity (e.g., subjects who are at risk for the transition from "stable/chronic" cardiovascular disease, such as stable angina, to "unstable/acute" disease cardiovascular disease, such as acute coronary syndrome) can be determined by measuring the level, distribution, and/or location of MRP-14 in blood, vasculature, or thrombus of the subject and correlating the measured distribution, and/or location of MRP-14 with an increased risk of hypercoagulation, thrombosis, and cardiovascular disease activity.

In some embodiments, the level, distribution, and/or location of MRP-14 can be measured by administering to the subject a molecular probe that includes an MRP-14 targeting peptide. The MRP-14 targeting peptide can have an amino acid sequence at least 80% identical to an amino acid sequence selected from the group consisting of SEQ ID NO: 2, SEQ ID NO: 3, SEQ ID NO: 5, SEQ ID NO: 6, SEQ ID NO: 9, and SEQ ID NO: 10. The molecular probes bound to MRP-14 in the subject's vasculature can then be detected to determine the location, and/or distribution of thrombus formation in the subject.

The measured level, distribution, and/or location of MRP-14 in the subject can be correlated to the presence of hypercoagulation, thrombosis, and/or cardiovascular disease activity in the subject, the increased likelihood or risk of hypercoagulation, thrombosis, and/or cardiovascular disease activity in the subject, and/or the severity of hypercoagulation, thrombosis, and/or cardiovascular disease activity in the subject by comparing the measured level with a reference or control level. An increase in the level, location, and/or distribution of MRP-14 compared to the control or reference level, location, and/or distribution can be indicative of the presence, increased risk, and/or severity of hypercoagulation, thrombosis, and/or cardiovascular disease activity in the subject.

Distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values may represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favorable or unfavorable prognoses for such disease or condition.

Such comparison may generally include any means to determine the presence or absence of at least one difference and optionally of the size of such different between values or profiles being compared. A comparison may include a visual inspection, an arithmetical or statistical comparison of measurements. Such statistical comparisons include, but are not limited to, applying a rule. If the values or biomarker profiles comprise at least one standard, the comparison to determine a difference in said values or biomarker profiles may also include measurements of these standards, such that measurements of the biomarker are correlated to measurements of the internal standards.

Reference values for the quantity, location, and/or distribution of MRP-14 may be established according to known procedures previously employed for other biomarkers.

For example, a reference value of the quantity, location, and/or distribution of MRP-14 in the vasculature indicative of the presence, increased risk, and/or severity of hypercoagulation, thrombosis, and/or cardiovascular disease activity in the subject may be established by determining the quantity, location, and/or distribution of MRP-14 from one individual or from a population of individuals characterized by the particular diagnosis, prediction and/or prognosis of said disease or condition (i.e., for whom said diagnosis, prediction and/or prognosis of hypercoagulation and/or thrombosis holds true).

Hence, by means of an illustrative example, reference values of the quantity of MRP-14 for the diagnoses of hypercoagulation, thrombosis, and/or cardiovascular disease activity vs. no hypercoagulation and/or thrombosis, and/or stable cardiovascular disease activity may be established by determining the quantity, location, and/or distribution of platelet MRP-14 from one individual or from a population of individuals diagnosed (e.g., based on other adequately conclusive means, such as, for example, clinical signs and symptoms, imaging, ECG, etc.) as, respectively, having or not having said disease or condition The expression level or presence of MRP-14 in a patient may sometimes fluctuate, i.e., increase or decrease significantly without change (appearance of, worsening or improving of) symptoms. In such an event, the marker change precedes the change in symptoms and becomes a more sensitive measure than symptom change. Therapeutic intervention can be initiated earlier and be more effective than waiting for deteriorating symptoms. Early intervention at a more benign status may be carried out safely at home, which is a major improvement from treating seriously deteriorated patients in the emergency room.

Measuring the MRP-14 of the same patient at different time points may in such a case thus enable the continuous monitoring of the status of the patient and may lead to prediction of worsening or improvement of the patient's condition with regard to a given disease or condition as taught herein. Alternatively, these reference values or ranges can be established through data sets of several patients with highly similar disease phenotypes, e.g., from healthy subjects or subjects not having the disease or condition of interest. A sudden deviation of the MRP-14 from said reference value or range can predict the worsening of the condition of the patient (e.g., at home or in the clinic) before the (often severe) symptoms actually can be felt or observed.

In some embodiments, compositions including MRP-14 targeting peptides described herein can be administered to subject with measured elevated MRP-14 levels compared to control levels that are indicative of the presence, increased risk, and/or severity of hypercoagulation, thrombosis, and/or cardiovascular disease activity in the subject. Such subjects as described herein can be prone to or suffers from a cardiovascular disease, such as acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures resulting from angioplasty, carotid endarterectomy, post CABG (coronary artery bypass graft) surgery, vascular graft surgery, stent placements and insertion of endovascular devices and prostheses.

The following example is included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

Example

In this Example, we identified peptide ligands for MRP-14 using combinatorial molecular biology technique of phage display. While MRP-14 antibodies have been produced, there are limitations to the clinical success of antibodies due to their high manufacturing cost, immunogenicity, large size, and nonspecific interactions of their Fc portion. Utilizing peptides and attaching them directly to thrombolytics or onto nanocarriers would address these issues; in particular, multivalent display of the peptides on nanocarriers would lead to greater specificity through avidity effects.

For the nanocarrier, a nature-inspired approach based on plant viruses was used. Virus-based particles are attractive for medical cargo delivery because they have evolved to survive many different physiological conditions and specifically release their cargos in cells. Plant viruses in particular are clinically relevant, as they can be nanomanufactured consistently and in high yields through molecular farming in plants and are biocompatible, biodegradable, and noninfectious in humans and animals. In particular, the 300 by 18 nm rod-shaped plant virus-based nanoparticle tobacco mosaic virus (TMV) was selected due to its unique hollow nanotube architecture, which has been demonstrated to confer greater thrombosis targeting properties for TMV. Elongated particles are recognized for more favorable margination properties due to a greater capacity for drifting laterally toward the vessel wall and enhanced vascular interaction upon encountering the disease site due to greater surface areas with better presentations of targeting ligands. Nevertheless, it remains technologically difficult to obtain large quantities of elongated materials of high uniformity at the nanoscale using purely synthetic approaches.

Materials and Methods

Determination of Phage Concentration

During phage display, the concentration of the phages was determined by titering on isopropyl β-D-thiogalactopyranoside/5-bromo-4-chloro-3-indolyl-beta-D-galacto-pyranoside (IPTG/X-gal) plates, counting the number of plaque-forming units (pfu), and scaling accordingly. After amplification of individual plaques, the concentration was determined by UV/visible spectroscopy using a NanoDrop spectrophotometer with a 1 mm path length according to the following equation: $(A_{269\ nm} A_{320\ nm})(6 \times 10^{17})$/number of bases.

Phage Display

Ph.D.-7 and Ph.D.-C7C phage display peptide libraries (New England Biolabs) were used to identify peptides specific for MRP-14 according to manufacturer's recommendations. Briefly, three rounds of solution-phase panning were performed. In the first round, phages from the library ($10^{11}$ pfu/mL) were incubated with His-tagged MRP-14 (2 pmol, Novus Biologicals) in 200 μL of TBST (0.1% (v/v) Tween 20) for 20 minutes at room temperature. The solution was then mixed for 15 minutes with 50 μL of HisPur Ni-nitrilotriacetic acid (NTA) resin slurry (Pierce) that had been blocked with bovine serum albumin (BSA). After washing 10 times with TBST, bound phages were eluted with 1 mL of 0.2 M glycine-HCl, pH 2.2 with 1 mg/ml BSA that was quickly neutralized with 150 μL of 1 M Tris-HCl, pH 9.1. Phage amplification was performed with ER2738 *E. coli*, and subsequent rounds of panning were performed with the amplified phages following the procedure above, except with TBST containing 0.5% Tween 20 and an additional negative selection step where the phages were first incubated with blocked resin for 15 minutes before transferring the supernatant for mixing with MRP-14. After the third round of panning, random phages specific for MRP-14 were selected for using blue-white screening, their DNA isolated, and their sequences determined using the −96 gIII sequencing primer (Eurofins Genomics).

Phage Enzyme-Linked Immunosorbent Assay (ELISA)

Phage specificity for MRP-14 was verified by performing an ELISA. Polysorp 96-well plates (Nunc) were coated with 50 μL of 50 μg/mL MRP-14 in 0.1 M NaHCO₃, pH 8.6 in a humidified chamber overnight at 4° C. The coated wells and additional wells for phage dilutions were blocked with 5 mg/mL BSA in 0.1 M NaHCO$_3$, pH 8.6 for 1 hour at 4° C. After washing 6 times with TBST (0.5% Tween 20), 8 serial fourfold dilutions from $10^{12}$ phages/mL down to 6×10$^7$ phages/mL were performed in blocked wells then 100 μL of the phages added to MRP-14-coated wells and incubated for 1 hour at room temperature. The wells were washed 6 times with TBST, then 100 μL of horseradish peroxidase (HRP)-conjugated anti-M13 monoclonal antibody (GE Healthcare) diluted 1:5000 in 2% dry milk in PBS was added to the wells. Another washing step with TBST 6 times was carried out. Finally, HRP activity was detected using 100 μL 2,2'-azino-bis(3-ethylbenzothiazoline-6-sulfonic acid) diammonium salt (ABTS) colorimetric substrate solution (Life Technologies) at room temperature for 30 minutes. Absorbance was measured at 410 nm using a Tecan Infinite 200 plate reader Surface Plasmon Resonance (SPR) Characterization Shortlisted MRP-14 targeting peptides (MTPs) were synthesized with a GGGS spacer and C-terminal amidation (Genscript) and their binding affinities characterized by SPR using Biacore T100 (GE Healthcare). PBST (0.05% Tween 20), pH 7.4 containing 50 ethylenediaminetraacetic acid (EDTA) was used as the running buffer. NTA sensor chips (GE Healthcare) were charged with 0.5 mM NiCl$_2$ solution for 2 minutes at a flowrate of 10 μL/min, then 10 μg/mL His-tagged MRP-14 was bound for 2 minutes at 10 μL/min. For testing affinity to MRP-8/14, untagged MRP-8 (Novus Biologicals) was premixed in a 1:1 ratio with His-tagged MRP-14 for 3 hours in the presence of 0.1 mM CaCl$_2$. Peptides at concentrations ranging from 6.25 μM to 100 μM diluted in running buffer were then injected at 30 μL/min for 1 minute association followed by 1 minute dissociation. Affinity was calculated by fitting a saturation binding curve to the equilibrium response vs. peptide concentration graph. For affinity of TMV-MTP6, concentrations ranging from 390.625 nM to 12.5 μM peptide were tested and affinity determined by kinetic curve fitting with the Biacore software.

TMV Propagation

Wild-type TMV was propagated in *Nicotiana benthamiana* tobacco plants and purified using established protocols. Yields of up to 500 mg/g infected leaf material were obtained.

TMV Conjugation

An alkyne handle was attached to the exterior of TMV (TMV-eAlk) by diazonium coupling. Diazonium salt was first formed by reacting 100 mM 3-ethynylaniline with 150 mM sodium nitrite in p-toluenesulfonic acid for 1 hour on ice in the dark. TMV was then incubated with 35 equivalents per coat protein of diazonium salt in 0.1 M borate buffer, pH 8.8 for 30 minutes on ice in the dark. The product and subsequent reactions were purified by ultracentrifugation over a sucrose cushion at 42,000 rpm for 3 hours. MTP6 with a terminal azide was synthesized with an intervening GGGS and polyethylene glycol (PEG) spacer (3 monomers) (JPT). The functionalized MTP6 was then attached to TMV-eAlk by copper(I)-catalyzed azide-alkyne cycloaddition (CuAAC) using 2 equivalents of MTP6-N$_3$ per TMV coat protein in a 2 mg/mL solution of TMV in 10 mM phosphate buffer, pH 7.4 and in the presence of 2 mM aminoguanidine, 2 mM ascorbic acid sodium salt, and 1 mM copper sulfate on ice for 30 minutes. To chelate the copper and stop the reaction, 5 mM EDTA was added for 5 minutes. To make dye-labeled particles, the interior of TMV was labeled with alkynes (TMV-iAlk) by adding 15 equivalents of propargylamine, 30 equivalents of hydroxybenzotriazole, and 30 equivalents of EDC (10 equivalents at 0, 6, and 18 hours) in 0.1 M HEPES buffer, pH 7.4 and reacting for 24 hours total before purifying. TMV-iAlk was then reacted with 3 equivalents of sulfo-Cyanine5 azide (sCy5) by CuAAC.

Gel Electrophoresis

SDS gel electrophoresis was performed with 10 μg TMV samples that were denatured at 100° C. for 5 minutes. The samples were run on a 4-12% NuPAGE gel (Invitrogen) in 1×MOPS running buffer at 200 V for 50 minutes. The gel was stained with Coomassie Blue and photographed using an AlphaImager system (Protein Simple). Lane analysis was performed using ImageJ software.

Transmission Electron Microscopy (TEM)

Samples were diluted to a concentration of 0.1 mg/mL in deionized water and applied to formvar carbon-coated grids (Electron Microscopy Sciences) for 5 minutes. After blotting away excess liquid, the grids were rinsed briefly with deionized water and then negatively stained with 2% uranyl acetate solution for 2 minutes. The samples were imaged at 200 kV with a Zeiss Libra 200FE microscope.

UV/Visible Spectroscopy

The concentrations of TMV and sCy5 were determined by the Beer-lambert law using an extinction coefficient ($\varepsilon_{260\,nm}$) of 3 mg$^{-1}$ mL cm$^{-1}$ and a molecular weight of 39.4 MDa for TMV and an extinction coefficient ($\varepsilon_{646\,nm}$) of 271,000 M$^{-1}$ cm$^{-1}$ for sCy5.

Ex Vivo Thrombus Formation

A perfusion chamber (Portola Pharmaceuticals) was used to evaluate the effect of particles on thrombus formation time. Factor Xa inhibitor anticoagulated blood was labeled with 5 Rhodamine 6G (Sigma-Aldrich) for 10 minutes. Particles were added at a final concentration of 50 μg/mL and then the blood perfused through human type III collagen-coated rectangular capillaries at an arterial shear rate of 600 s$^-$. Thrombus formation under flow was then visualized in real time and average fluorescence of platelet aggregation over time quantified.

Photochemical Injury Mouse Model

All animal procedures were performed according to approved protocols from the Institutional Animal Care and Use Committee at Case Western Reserve University. 8-9 week old male C57BL/6 mice were anesthetized by intraperitoneal injection of 62.5 mg/kg sodium pentobarbital. After anesthesia, peptide-targeted and untargeted TMV particles (200 μg/100 μL) were injected intravenously followed by dissection of the mice to expose the right common carotid artery. Rose Bengal dye (10 mg/mL in PBS) was then administered via tail vein injection and a 540 nm green laser light (1.5 mW, Melles Griot) placed 5 cm from the artery was used to stimulate photochemical injury and induce thrombus formation. A Doppler flow probe (Transonic Systems) was placed under the artery and used to monitor blood flow. The mice were sacrificed after vessel occlusion. The artery and the contralateral control were excised and fixed in formalin, then imaged by Maestro fluorescence imaging to determine targeting of the particles (see below). Additionally, to study the biodistribution of the particles, the brain, heart, lungs, kidneys, spleen, and liver were also excised and imaged with Maestro imager.

Maestro Ex Vivo Imaging

The red fluorescence from sCy5 was imaged using Maestro imager, with 800 ms exposure time for the arteries and 400 ms exposure time for the organs. The signal was filtered with 576 to 621 nm excitation and 635-nm longpass emission filters.

Results
Identification of Peptides Specific for MRP-14

Peptides with affinity to MRP-14 were selected for through three rounds of solution-phase panning, using both linear and cyclic phage display peptide libraries based on bacteriophage M13 from New England Biolabs. After incubation with the phage library, His-tagged MRP-14 was captured using Ni-nitrilotriacetic acid (NTA) beads to isolate bound phages. The captured phages were then amplified for the next round of panning Blue-white screening of the third round phages was performed, and 30 plaques were sequenced from the linear library and 31 plaques from the cyclic library. The different MRP-14 targeting peptide (MTP) sequences identified and their frequencies can be found in Table 1. A common motif between the various sequences is the presence of several histidine residues. The recurrence of the positively charged residue indicates that the MRP-14 binding site is shared between the identified peptides, possibly coinciding with one of its calcium-binding domains.

TABLE 1

Peptide sequences identified through phage display

| Linear Ph.D.-7 Library | | | Cyclic Ph.D.-C7C Library | | |
|---|---|---|---|---|---|
| Label | Sequence | Frequency | Label | Sequence | Frequency |
| MTP1 | TTFHHHK (SEQ ID NO: 1) | 2 | MTP4 | ACKAPAHHHC (SEQ ID NO: 4) | 1 |
| MTP2 | ASSHIHH (SEQ ID NO: 2) | 26 | MTP5 | ACNSHRHGAC (SEQ ID NO: 5) | 15 |
| MTP3 | HNHMADP (SEQ ID NO: 3) | 2 | MTP6 | ACNSVHQHHC (SEQ ID NO: 6) | 11 |
| | | | MTP7 | ACYGKPEHHC (SEQ ID NO: 7) | 1 |
| | | | MTP8 | ACPHHPQKHC (SEQ ID NO: 8) | 1 |
| | | | MTP9 | ACPTGLHHAC (SEQ ID NO: 9) | 1 |
| | | | MTP10 | ACRPKNNHSC (SEQ ID NO: 10) | 1 |

To narrow down the peptide library to the ones with highest affinity, an enzyme-linked immunosorbent assay (ELISA) was performed with the isolated phages. ELISA plates were coated with MRP-14 then incubated with varying concentrations of each phage, ranging from $6 \times 10^7$ to $10^{12}$ phages/mL. Bound phage was detected using horseradish peroxidase (HRP)-labeled anti-M13 antibodies followed by addition of 2,2'-azino-bis(3-ethylbenzothiazoline-6-sulfonic acid) diammonium salt (ABTS) substrate (FIG. 1). Specificity for MRP-14 was confirmed by high binding of the phages to MRP-14 but not bovine serum albumin (BSA), which was used for blocking. Additionally, unlabeled M13 did not show affinity for MRP-14, indicating the binding of the phages is conferred by the peptide displayed. Based on the phage ELISA results, six peptides were selected for further analysis: MTP2, MTP3, MTP5, MTP6, MTP9, and MTP10 with sequences ASSHIHH (SEQ ID NO: 2), HNHMADP (SEQ ID NO: 3), ACNSHRHGAC (SEQ ID NO: 5), ACNSVHQHHC (SEQ ID NO: 6), ACPTGLHHAC (SEQ ID NO: 9), and ACRPKNNHSC (SEQ ID NO: 10), respectively.

The peptides were synthesized with a glycine GGGS spacer at the C-terminus along with C-terminal amidation to best match their structure and charge when displayed on M13. Their binding affinity to MRP-14 was then quantified using surface plasmon resonance (SPR) with an NTA sensor chip. After charging with $Ni^{2+}$, His-tagged MRP-14 was immobilized on the chip. Then, binding of peptides with concentrations from 6.25 µM to 100 µM was evaluated and their dissociation constant ($K_d$) determined through saturation binding curve fitting (FIG. 2 and Table 2). The peptide with the strongest affinity was MTP6 (ACNSVHQHHC (SEQ ID NO: 6)), with the lowest $K_d$ of 39.6 µM. While the two strongest binders were cyclic (MTPS and MTP6), the two linear peptides evaluated (MTP2 and MTP3) were comparable, with only a factor of 2-3 difference in affinity. On the other hand, the other two cyclic peptides tested (MTP9 and MTP10) demonstrated differing behaviors from the other peptides, although we did not investigate them further due to low binding affinities displayed. MTP9 may have multiple binding sites on MRP-14, as there was a quick initial interaction followed by a slower binding phase. On the other hand, MTP10 did not really associate with MRP-14 and there was very little response observed with the SPR sensorgrams. From the phage ELISA, it was one of the best peptides, but it may be the case that it requires a different conformation of MRP-14 that was only present when the protein was coated on the ELISA plate.

Although the affinity of the lead peptide, MTP6, was only moderate, the fast association profile (see FIG. 2) would be beneficial for binding under flow for applications in vascular disease. Additionally, binding to MRP-14 can be improved through multivalent peptide display on a nanocarrier.

TABLE 2

Values for dissociation constants from SPR measurements with MRP-14

| Label | Sequence | $K_d$ (µM) |
|---|---|---|
| Scrambled | MDPHAHNGGGS (SEQ ID NO: 11) | no binding |
| MTP2 | ASSHIHHGGGS (SEQ ID NO: 12) | 77.6 |
| MTP3 | HNHMADPGGGS (SEQ ID NO: 13) | 116.8 |
| MTP5 | ACNSHRHGACGGGS (SEQ ID NO: 14) | 67.6 |
| MTP6 | ACNSVHQHHCGGGS (SEQ ID NO: 15) | 39.6 |
| MTP9 | ACPTGLHHACGGGS (SEQ ID NO: 16) | 190.9 |
| MTP10 | ACTPKNNHSCGGGS (SEQ ID NO: 17) | 191.0 |
| MTP6-$N_3$ | | 55.7 |
| TMV-MTP6 | | 0.754 |

Figure 3A:
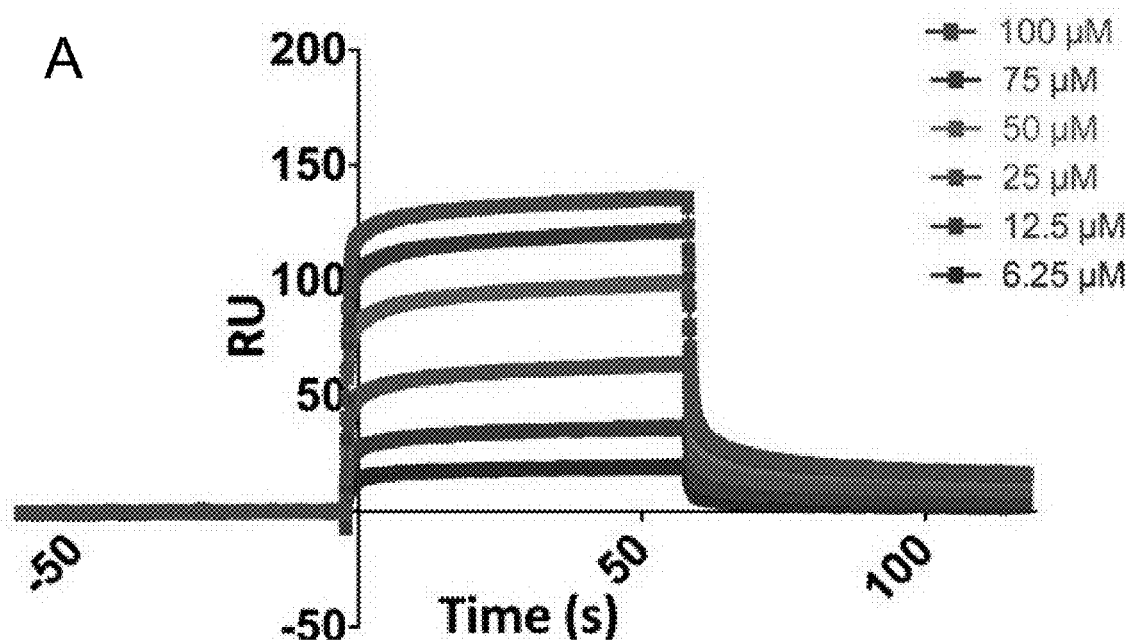
FIGS. 3(A-B) illustrate plots showing SPR analysis of MTP6 binding to MRP-8/14. SPR sensorgram data for peptide binding to immobilized MRP-8/14 (left) and determination of the dissociation constant using a rectangular hyperbola fit of the saturation binding curve (right).
Figure 3B:
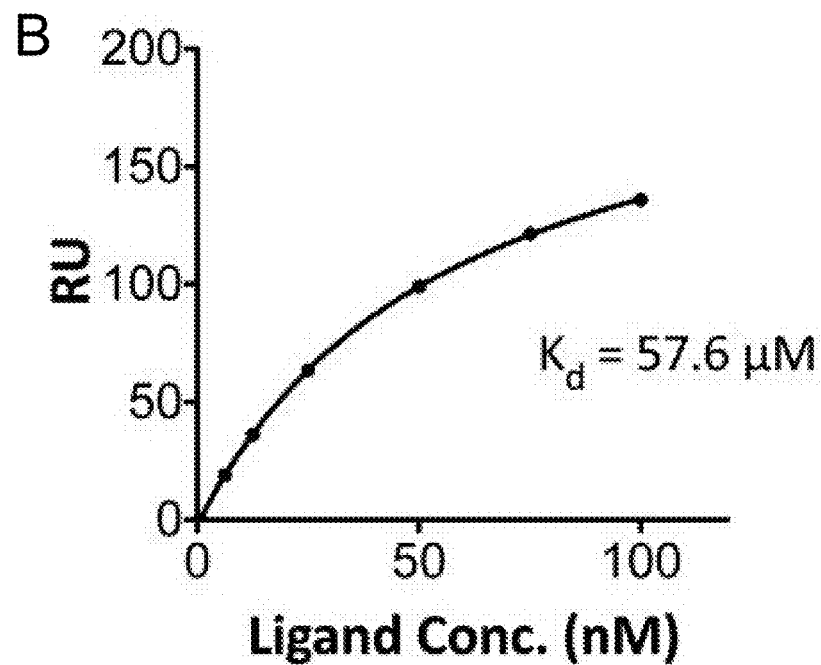

Since MRP-14 in vivo predominantly exists as a heterodimer with MRP-8, binding of MTP6 to MRP-8/14 was also investigated by SPR (FIG. 3). MRP-8/14 was formed by mixing equal molar concentrations of MRP-8 with MRP-14, with only MRP-14 having a His tag Immobilization of MRP-8/14 was performed under the same conditions as for MRP-14 and a response of 3600 response units (RU) was observed, which when compared to a response of around 1800 RU for MRP-14 alone indicated successful dimerization of MRP-8/14. For the association of MTP6 with MRP-8/14, the $K_d$ was determined to be 57.6 µM, with similar response curves as observed for MRP-14. Therefore, heterodimer formation does not appear to interfere with binding of the peptide. To further utilize MTP6 for display on a nanoparticle, MTP6-N$_3$ was synthesized with a short, 3-monomer polyethylene glycol (PEG) spacer and an azide group added to the C-terminus (see FIG. 4A). The additional functionality imparted on the peptide did not significantly affect its binding to MRP-14, with a $K_d$ observed of 55.7 µM (see FIG. 2 and Table 2).

Multivalent Display on TMV

Figure 4A:
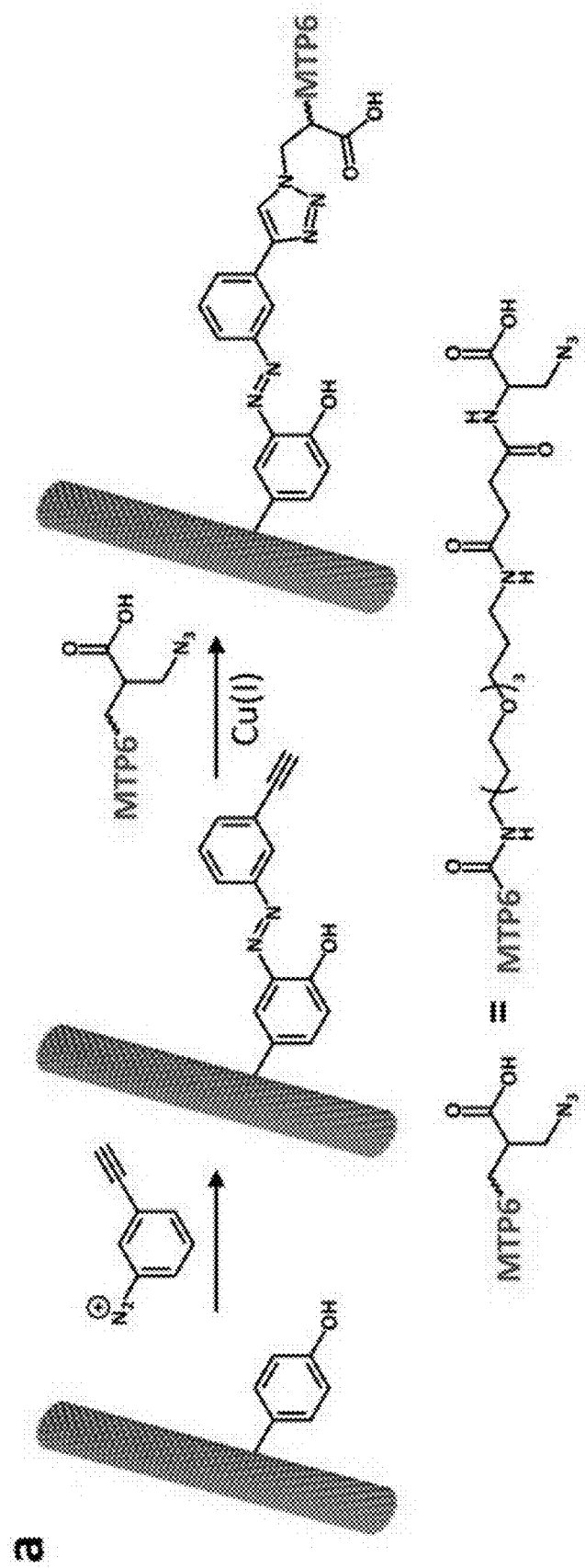
FIGS. 4(A-D) illustrate conjugation and characterization of TMV-MTP6. A) Schematic for the conjugation of MTP6 to TMV using CuAAC. B) SDS denaturing gel of TMV and TMV-MTP6 showed successful TMV modification. Conjugation of MTP6 to TMV coat proteins resulted in lower mobility in the gel and the presence of an additional band (arrow) on top of the unmodified coat protein band. C) TEM image of TMV-MTP6, which shows that the particles remained intact during modification. D) SPR sensorgram for binding of TMV-MTP6 to immobilized MRP-14. The dissociation of TMV-MTP6 from the sensor chip is much slower than previously found for MTP6, and based on kinetic fitting the $K_d$ is 0.754 μM. One of two similar experiments is shown.

The azide-functionalized MTP6 was attached to the exterior of TMV using established bioconjugation protocols where an alkyne handle was first attached to TMV tyrosine residues through diazonium coupling, then copper(I)-catalyzed azide-alkyne cycloaddition (CuAAC) was used to incorporate the peptide (FIG. 4A). MTP6 attachment was verified by SDS denaturing gel electrophoresis, and particle integrity was verified by transmission electron microscopy (TEM) (FIG. 4B, C). Densitometric analysis indicated about 20% modification of the TMV coat proteins (2130 total), or approximately 400 MTP6 attached per particle. Additionally, TEM revealed that the particles remained intact during modification.

Figure 4D:
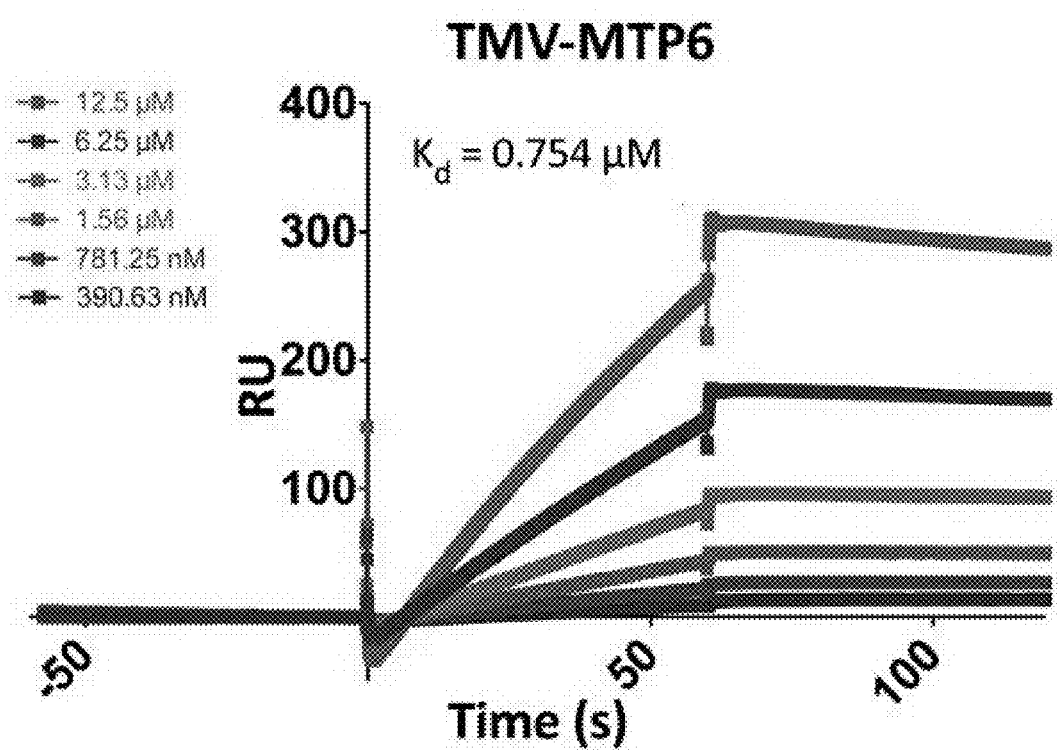

To determine how multivalent display of MTP6 on TMV affects its affinity to MRP-14, SPR analysis was performed for TMV-MTP6 using concentrations corresponding to 390.625 nM to 12.5 µM of MTP6 (FIG. 4D). Based on the sensorgrams, TMV-MTP6 has a high binding affinity with a much slower dissociation rate than MTP6 alone (compare with FIG. 2). The association and dissociation rates can only be compared qualitatively based on the sensorgram data due to the rates for the free peptides being too quick for the instrument to be able to determine their values. Kinetic fitting of the TMV-MTP6 data revealed that it has a $K_d$ of 0.754 µM ($k_a$=909.6 M$^{-1}$ s$^{-1}$ and $k_d$=6.858×10$^{-4}$ s$^{-1}$), about 2 orders of magnitude lower than what was found for MTP6. The higher affinity can be attributed to the cooperativity effect from display of multiple peptides on a single carrier. It is interesting to note that while the slower dissociation rate was expected, there was also a slower association rate observed as well. The momentum of the TMV under flow may contribute to the slower binding rate of the particle compared to the free peptide. Nevertheless, overall the multivalent display of the peptides on TMV resulted in a higher affinity.

Evaluation of Targeted Particles Ex Vivo and In Vivo

Figure 5A:
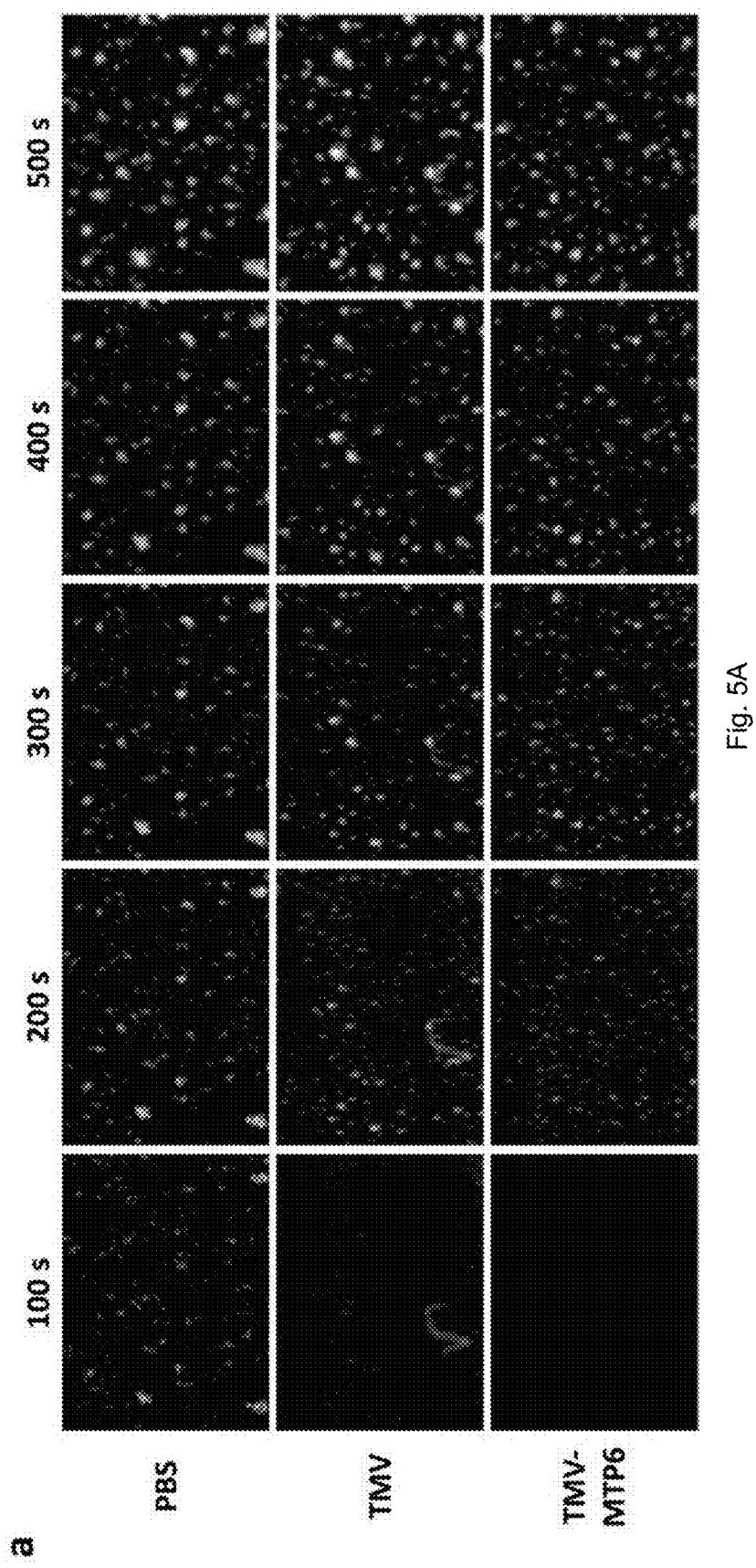
FIGS. 5(A-C) illustrate behavior of TMV-MTP6 ex vivo and in vivo. A) Comparison of the effect of TMV and TMV-MTP6 on shear-induced thrombus formation over time in an ex vivo flow chamber using blood labeled with Rhodamine 6G. One of two similar experiments is shown. B) Corresponding profiles quantifying the average pixel intensity of the aggregates over time show no significant effect on thrombosis. C) Maestro fluorescence imaging of carotid arteries (n=3) after photochemical injury revealed targeted TMV-MTP6 attachment to the thrombi and no nonspecific accumulation in the contralateral, uninjured artery.
Figure 5B:
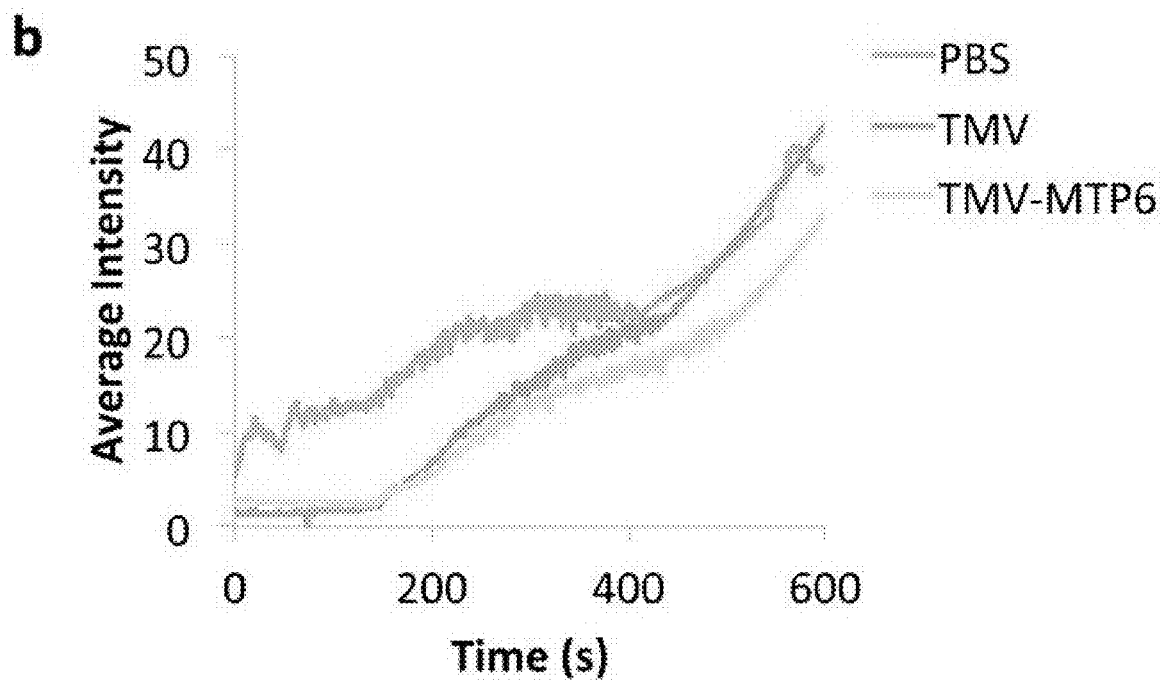

To verify that the particles do not aggregate or otherwise react poorly in blood and also obtain insight of the behavior of TMV-MTP6 under shear-induced thrombosis, the effect of the targeted particles on thrombosis was first tested ex vivo with anticoagulated blood using a laminar flow chamber. This model has previously been shown to mimic features of thrombosis and yielded variation in thrombosis progression when the activity of MRP-14 was modulated. Perfusion of blood through a collagen-coated capillary tube at an arterial shear rate of 600 s$^{-1}$ resulted in rapid formation of platelet thrombi over the course of 10 minutes. Particles were added before perfusion at a concentration of 50 µg/mL, and visualization of thrombus formation was achieved through fluorescence signal from cells labeled with Rhodamine 6G (FIG. 5A). After imaging, average pixel intensity of platelet aggregates over time was quantified (FIG. 5B). There was some delay in thrombus onset with the addition of both TMV and TMV-MTP6 compared to the PBS only control, likely due to some hindrance from the presence of the particles, but in general the thrombosis profiles were similar between the three conditions. Therefore, while MTP6 does not appear to block involvement of MRP-14 in thrombosis, there was also no detrimental effect observed from the multivalent display of MTP6 on TMV leading to crosslinking between activated platelets. This is a concern when using nanoparticles to target coagulation factors such as platelets and fibrin due to potential incorporation into the coagulation cascade and further aggregation, as illustrated by the use of such particles for mediating hemostasis. Since this is not the case for TMV-MTP6, it could then be investigated as platform for diagnostic imaging of thrombosis.

As an initial step, TMV and TMV-MTP6 were labeled with sulfo-Cyanine5 (sCy5) for optical imaging of targeting in a mouse thrombosis model. sCy5-azide was attached using CuAAC following EDC coupling to functionalize the interior glutamic acids of TMV with alkynes. Dye attachment after purification was verified by UV/visible spectroscopy, with similar labeling of around 300 dyes per particle.

Figure 5C:
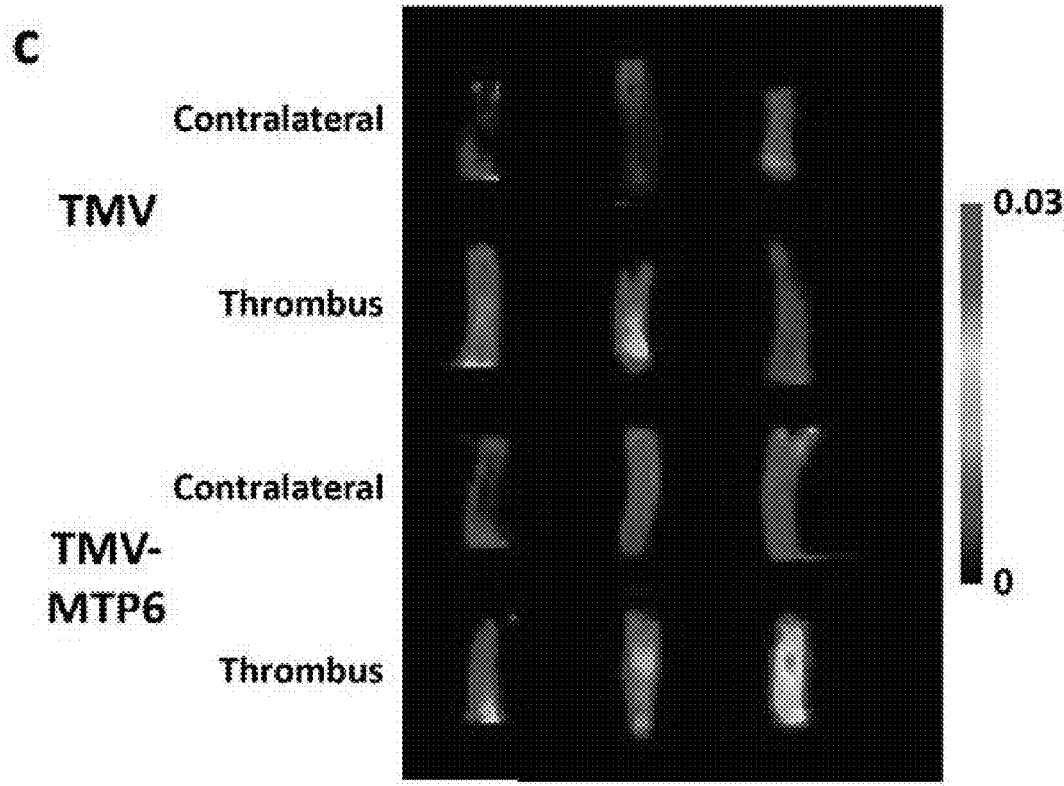

Progressing to the mouse model, the particles were first injected intravenously, then thrombosis was induced through photochemical injury of the carotid artery, specifically through reactive oxygen species formation from the reaction of green laser light with injected Rose Bengal dye. A flow probe was used to monitor the development of thrombosis, and the arteries along with their contralateral control were excised following occlusion of the vessel. Maestro ex vivo imaging for detecting particle localization within the arteries revealed some success with imaging thrombi in the three TMV-MTP6 mice, with one in particular showing the highest signal intensity (FIG. 5C). One mouse treated with TMV showed moderate signal, but qualitatively TMV-MTP6 imparted more specificity. Quantitatively, there was too much variation in intensity between the three mice to result in statistically significant differences between TMV and TMV-MTP6. Further investigation comparing the two formulations is needed to confirm TMV-MTP6 targeting. Additionally, sectioning and staining of the arteries to verify colocalization with MRP-14 would give more insight into the specificity of the thrombus targeting. In this pilot study, TMV-MTP6 was injected prior to induction of thrombosis. The quick initial clearance of TMV, with a half-life of 3.5 minutes, likely detracted from efficient targeting. Since in practice the thrombus would already be present before imaging agent injection, a better model would be to wait for the thrombus to reach a specific size before particle injection.

Figure 6A:
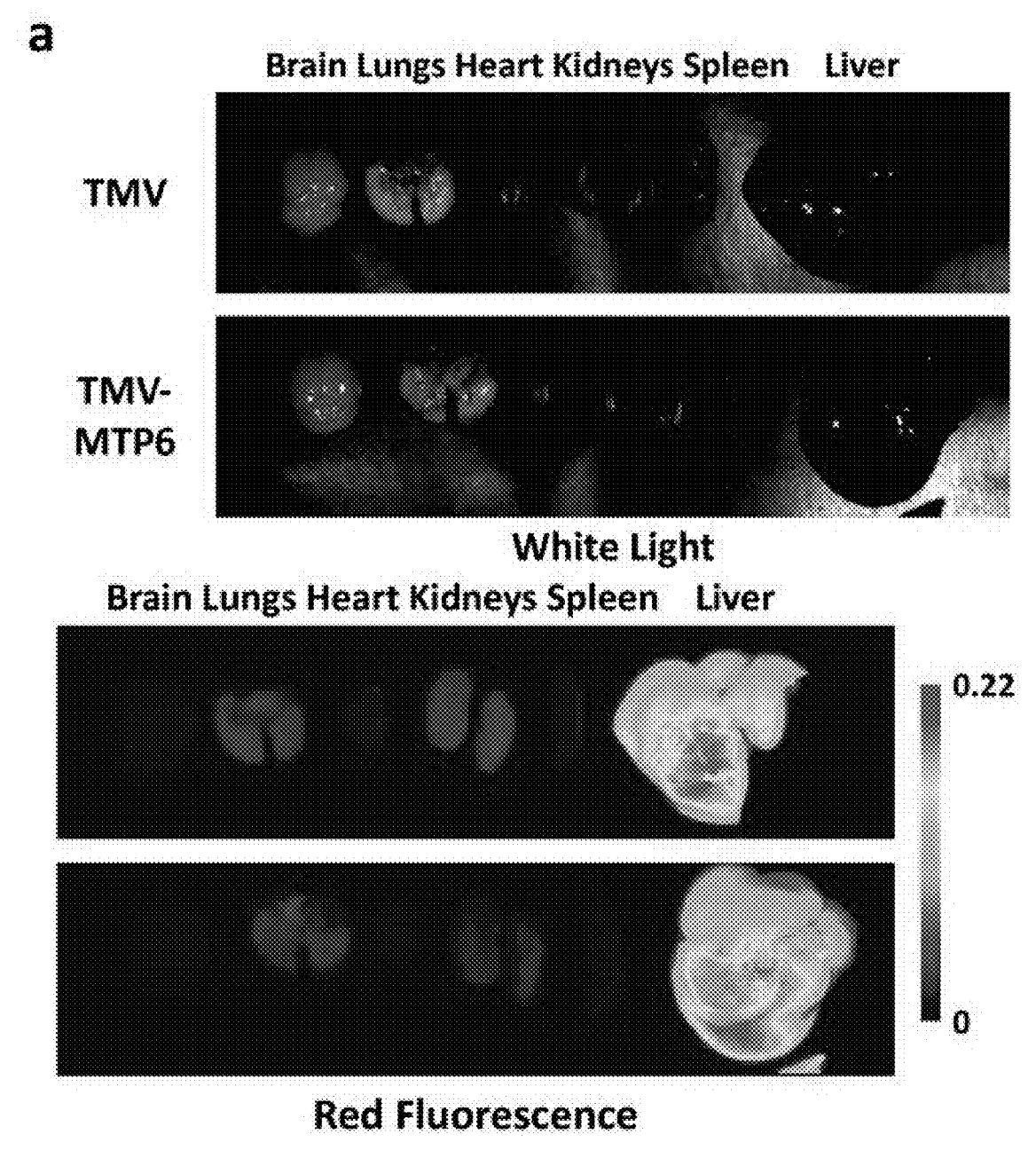
Figure 6B:
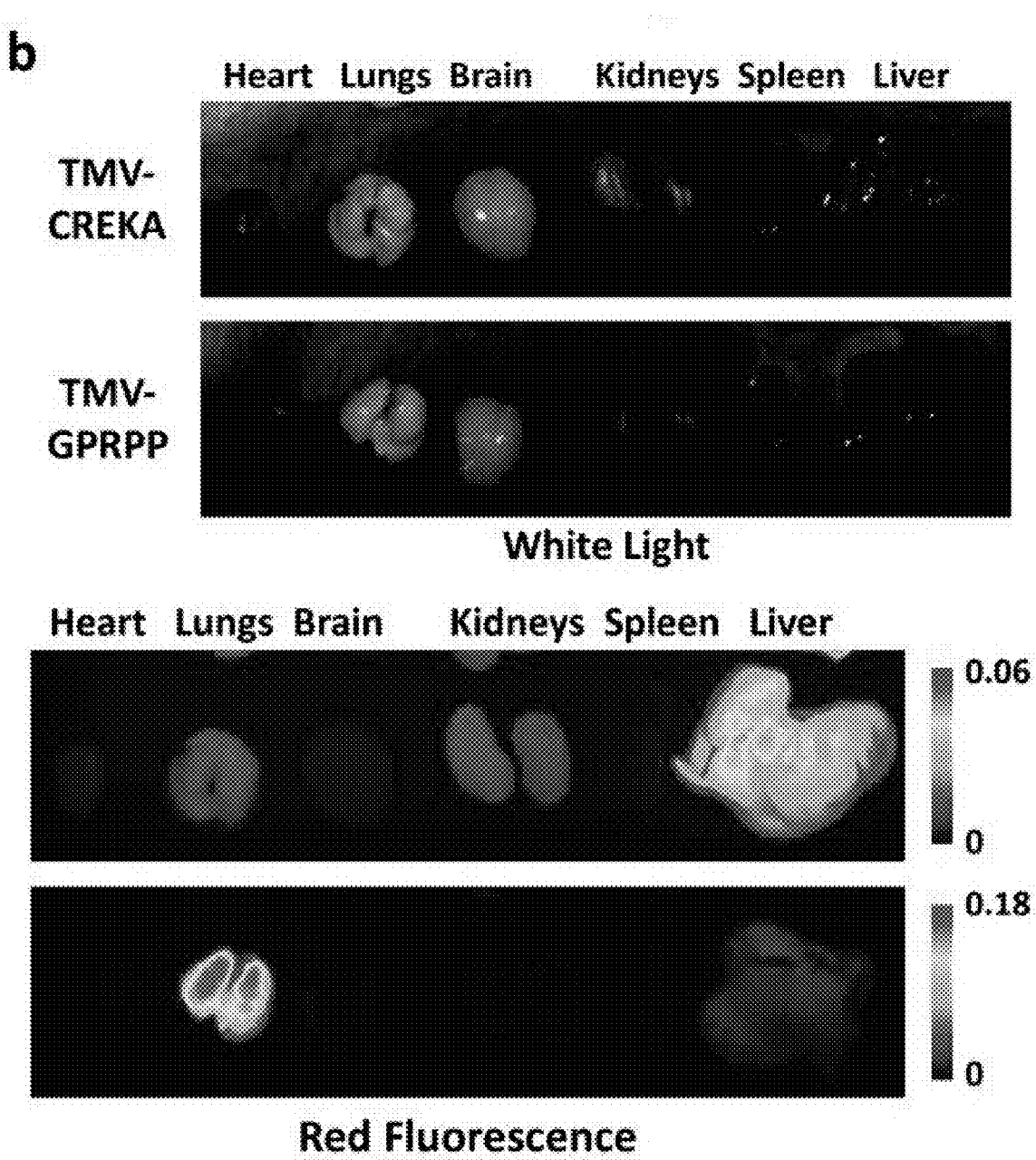
FIGS. 6(A-B) illustrate images showing biodistribution of various TMV formulations. A) Biodistribution was investigated by fluorescence imaging, with similar clearance behavior of TMV and TMV-MTP6. B) Biodistribution data for comparison of previously tested particles displaying CREKA and GPRPP peptides with specificity for fibrin demonstrate abnormal biodistribution of GPRPP-labeled particles. Dataset comes from previous study, with unpublished images from another set of mice shown.

Biodistribution was investigated concurrently with the photochemical injury model. The brain, lungs, heart, kidneys, spleen, and liver were collected and particle clearance examined through Maestro imaging (FIG. 6A). TMV and TMV-MTP6 had similar profiles, with clearance predominantly through the liver, which is the expected route of clearance for TMV and consistent with the pattern of nanoparticle clearance in general. From our first iteration particles that targeted fibrin for thrombus imaging, it was clear that protein corona formation on the particles had a significant impact on their in vivo behavior and biodistribution (FIG. 6B). Display of a specific peptide on TMV, GPRPP, was shown to interact with fibrinogen in blood plasma, which resulted in aggregate formation. The aggregates resulted in accumulation in the lungs, which was attributed to filtration through lung capillaries along with uptake by lung macrophages. In the case of MTP6, aggregate formation was not observed with the ex vivo thrombosis model above, and biodistribution further confirmed TMV-MTP6 is well behaved after systemic injection. TMV-MTP6 is then a good potential candidate that warrants further investigation for the detection of thrombosis.

In summary, we investigated a nanoparticle platform that shows a favorable profile for the development of imaging agents for thrombosis. Peptides specific for MRP-14 were successfully identified, and multivalent display of the highest affinity MTP6 peptide sequence ACNSVHQHHC (SEQ ID NO: 6) ($K_d$=39.6 µM) on rod-shaped TMV nanoparticles resulted in slower dissociation from MRP-14 and enhancement in the binding affinity ($K_d$=0.754 µM). The TMV-MTP6 particles behaved well, with no aggregation observed and no stimulation of thrombosis, when first tested in an ex vivo flow model, and targeting was observed when applied intravenously in an in vivo photochemical injury mouse model of thrombosis. Future work will further characterize the particles to verify thrombosis targeting by expanding the study to more mice to achieve greater power. Localization of the particles within the thrombus will also be examined through sectioning and immunofluorescence imaging to determine whether the particles are associated with platelets and MRP-14. With confirmation of MTP6 targeting of MRP-14 in vivo, there is also the potential to explore the application of MRP-14 targeting for diagnostics in models of atherosclerosis. Additionally, while using the nanoparticle confers multivalency and tunable pharmacokinetics, it would be advantageous for more rapid clinical translation to investigate the development of the peptide alone in the absence of a nanocarrier for the targeted delivery of contrast agents or therapeutics.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A composition for targeting MRP-14 comprising: an MRP-14 targeting peptide, the MRP-14 targeting peptide consisting of an amino acid sequence selected from the group consisting of SEQ ID NO: 2, SEQ ID NO: 3, SEQ ID NO: 5, SEQ ID NO: 6, SEQ ID NO: 9, and SEQ ID NO: 10.

2. The composition of claim 1, further comprising an imaging agent that is conjugated directly or indirectly to the targeting peptide.

3. The composition of claim 1, further comprising a nanocarrier, the targeting peptide being linked to the nanocarrier.

4. The composition of claim 3, wherein the nanocarrier includes a plant virus particle or virus like particle.

5. The composition of claim 4, wherein the plant virus particle or virus like particle is a rod-shaped virus particle.

6. The composition of claim 5, wherein the rod-shaped virus is a tobacco mosaic virus.

7. The composition of claim 2, wherein the imaging agent is detectable by at least one of gamma imaging, positron emission tomography (PET) imaging, computer tomography (CT) imaging, magnetic resonance imaging, near infrared imaging, or fluorescent imaging.

8. The composition of claim 1, further comprising a thrombolytic agent and/or anticoagulant.

9. A method of detecting thrombus formation in a subject in need thereof, the method comprising:
administering to the subject a molecular probe, the molecular probe comprising an MRP-14 targeting peptide, the MRP-14 targeting consisting of an amino acid sequence selected from the group consisting of SEQ ID NO: 2, SEQ ID NO: 3, SEQ ID NO: 5, SEQ ID NO: 6, SEQ ID NO: 9, and SEQ ID NO: 10, and detecting the molecular probes bound to MRP-14 in the subject's vasculature to determine the location, and/or distribution of thrombus formation in the subject.

10. The method of claim 9, the molecular probe further comprising an imaging agent that is conjugated directly or indirectly to the targeting peptide.

11. The method of claim 9, further comprising a nanocarrier, the targeting peptide being linked to the nanocarrier.

12. The method of claim 11, wherein the nanocarrier includes a plant virus particle or virus like particle.

13. The method of claim 12, wherein the plant virus particle or virus like particle is a rod-shaped virus particle.

14. The method of claim 13, wherein the rod-shaped virus is a tobacco mosaic virus.

15. The method of claim 11, wherein the imaging agent is detectable by at least one of gamma imaging, positron emission tomography (PET) imaging, computer tomography (CT) imaging, magnetic resonance imaging, near infrared imaging, or fluorescent imaging.

16. The method claim 9, wherein the subject is prone to or suffers from a cardiovascular disease.

17. The method of claim 16, wherein the cardiovascular disease is at least one selected from the group consisting of acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures resulting from angioplasty, carotid endarterectomy, post CABG (coronary artery bypass graft) surgery, vascular graft surgery, stent placements and insertion of endovascular devices and prostheses.

18. A composition comprising:
a plant virus particle or virus like particle,
a plurality of MRP-14 targeting peptides conjugated to the plant virus particle or virus like particle, the MRP-14 targeting peptide consisting of an amino acid sequence selected from the group consisting of SEQ ID NO: 2, SEQ ID NO: 3, SEQ ID NO: 5, SEQ ID NO: 6, SEQ ID NO: 9, and SEQ ID NO: 10.

19. The composition of claim 18, further comprising at least one imaging agent or therapeutic agent conjugated to the plant virus particle or virus like particle.

20. The composition of claim 18, wherein the plant virus particle or virus like particle is a rod-shaped plant virus particle or virus like particle.

21. The composition of claim 18, wherein at least 200 MRP-14 targeting peptides are conjugated to the plant virus particle or virus like particle.

* * * * *